(12) United States Patent
Mayor et al.

(10) Patent No.: US 7,580,127 B1
(45) Date of Patent: Aug. 25, 2009

(54) POLARIZATION LIDAR FOR THE REMOTE DETECTION OF AEROSOL PARTICLE SHAPE

(75) Inventors: Shane Mayor, Boulder, CO (US); Scott Spuler, Westminster, CO (US)

(73) Assignee: University Corporation for Atmospheric Research, Boulder, CO (US)

( * ) Notice: Subject to any disclaimer, the term of this patent is extended or adjusted under 35 U.S.C. 154(b) by 229 days.

(21) Appl. No.: 11/459,267

(22) Filed: Jul. 21, 2006

(51) Int. Cl.
*G01N 21/00* (2006.01)
(52) U.S. Cl. .................... 356/337; 356/341
(58) Field of Classification Search .......... 356/335–343
See application file for complete search history.

(56) References Cited

U.S. PATENT DOCUMENTS

| | | | | |
|---|---|---|---|---|
| 3,653,767 A * | 4/1972 | Liskowitz | ............... | 356/336 |
| 3,788,742 A * | 1/1974 | Garbuny | ............... | 356/5.03 |
| 3,925,666 A * | 12/1975 | Allan et al. | ............ | 250/338.5 |
| 4,636,075 A * | 1/1987 | Knollenberg | .......... | 356/336 |
| 4,854,705 A * | 8/1989 | Bachalo | .................. | 356/336 |
| 5,206,698 A | 4/1993 | Werner et al. | | |
| 5,241,315 A * | 8/1993 | Spinhirne | ............... | 342/54 |
| 5,414,723 A * | 5/1995 | Krapchev | .............. | 372/3 |
| 5,502,561 A * | 3/1996 | Hutchins et al. | ........ | 356/336 |
| 5,574,553 A | 11/1996 | McManamon et al. | | |
| 5,610,704 A * | 3/1997 | Berzins et al. | .......... | 356/28.5 |
| 5,815,250 A | 9/1998 | Thomson et al. | | |
| 5,875,029 A * | 2/1999 | Jann et al. | .............. | 356/511 |
| 6,052,187 A | 4/2000 | Krishnan et al. | | |
| 6,069,565 A | 5/2000 | Stern et al. | | |
| 6,320,651 B1 | 11/2001 | Manhart et al. | | |
| 6,404,494 B1 * | 6/2002 | Masonis et al. | .......... | 356/338 |
| 6,448,923 B1 | 9/2002 | Zrnic et al. | | |
| 6,490,530 B1 * | 12/2002 | Wyatt | ..................... | 702/24 |
| 6,556,282 B2 * | 4/2003 | Jamieson et al. | ........ | 356/4.01 |
| 6,608,669 B2 | 8/2003 | Holton | | |
| 6,839,141 B2 * | 1/2005 | Hill | ........................ | 356/486 |
| 7,151,787 B2 * | 12/2006 | Kulp et al. | .............. | 372/70 |
| 2003/0197863 A1 * | 10/2003 | Snelling et al. | .......... | 356/337 |

* cited by examiner

*Primary Examiner*—Gregory J Toatley, Jr.
*Assistant Examiner*—Jarreas C Underwood
(74) *Attorney, Agent, or Firm*—Marsh Fischmann & Breyfogle LLP

(57) ABSTRACT

A polarization lidar system capable of remotely identifying characteristics of atmospheric aerosol particles by transmitting a polarized beam of light and analyzing polarization characteristics of received backscatter is disclosed. The transmitter features high pulse energy to remotely identify aerosol particles with substantially one pulse. The transmitter employs a thin film plate polarizer and a Raman wavelength shifter to achieve eye-safe, single-plane linearly polarized energy. The transmit beam and receiver field of view are coaxial. The receiver employs a telescope, a collimating lens, and a beam splitter. The beam splitter splits the received backscatter into a single-plane polarized beam whose polarization plane is parallel to the plane of transmission and a single-plane polarized beam whose polarization plane is perpendicular to the plane of transmission. Each split beam is directed through separate focusing lenses onto separate detectors. The detector signals are amplified and processed to remotely determine atmospheric aerosol particle characteristics.

49 Claims, 13 Drawing Sheets

POLARIZATION LIDAR FOR THE REMOTE DETECTION OF AEROSOL PARTICLE SHAPE

GOVERNMENT SUPPORT

The present invention was made with Government support under Cooperative Agreement No. ATM-0301213 awarded by the National Science Foundation. The Government has certain rights in this invention.

FIELD OF THE INVENTION

This invention relates to laser radars or lidars in general and more particularly to a lidar system suitable for defense, scientific, environmental and commercial applications requiring long range remote identification of aerosol particles.

BACKGROUND OF THE INVENTION

The remote identification of aerosol particles is critical in many different applications. Of primary importance is the remote identification of chemical, radiological or biological agents in the atmosphere. In modern times the potential of intentional releases of a biological, chemical or radiological contaminants into the atmosphere is a real and serious threat to civilian populations in the United States and abroad and also to military personnel throughout the world. It would be extremely beneficial to be able to identify and track such aerosol particles remotely. The identification information could be used to initiate proper safety precautions and to identify the source of the aerosol particles.

Another critical application for remote aerosol particle identification is in the field of environmental science. Knowing the location and composition of aerosol particles can assist in many ways. For example, environmental regulators could detect sources of particulate matter in densities too low for visual identification. By analyzing the motion of the aerosol distribution over time, wind vectors can be determined. This data could then be used to determine possible sources of the aerosol particles along with potential future distribution of the aerosol particles. Environmental regulators could also use aerosol particle identification to determine the composition of plumes emanating from industrial facilities. In the case of a plume that poses an immediate or long-term health risk, the data would be valuable to health officials and researchers. Tracking the behavior of plumes of aerosol particles and determining the constituents of plumes of aerosol particles could also be valuable to meteorologists and researchers studying the effects of pollution on global warming and climate behavior.

Current methods of remotely obtaining information about aerosol particles are limited in their capabilities. Generally, these systems transmit laser energy into the atmosphere and detect returned radiation for analysis to identify particle aggregations and atmospheric structure of interest. The laser energy is transmitted into the atmosphere in the form of laser pulses. After a short laser pulse the system monitors for returned radiation. The delay between the time the pulse was initiated and the time the return radiation was received indicates the distance from the transmitter of the particles that caused the radiation to be returned.

The measurement of depolarization characteristics has been used to determine the state of water clouds in the atmosphere. In this method, linearly polarized light is transmitted into the atmosphere and the backscatter is examined for out-of-plane backscattered radiation. A low amount of out-of-plane backscattered radiation indicates that the water vapor is in liquid form. A higher amount of out-of-plane backscattered radiation indicates that the water particles exist in the form of ice crystals. Known depolarization measurement systems use primary wavelengths significantly shorter than 1.5 microns. Due to the wavelengths used by known systems, this method is either non eye-safe, in that the transmitted optical beams used do not meet critical safety standards and therefore extraordinary safety precautions are required, or the method is used at such a low power as to be eye-safe. However, in this low-power mode the system must time-average the backscatter information over a significant period of time resulting in long measurement times. This is generally achieved by incorporating photon-counting receivers. These long measurement times also prevent known eye-safe systems from scanning the atmosphere in a timely manner. Rapid scanning is important in order to create coherent time-lapse animations of the data, which reveal characteristics of the atmospheric flow and dispersion.

SUMMARY OF THE INVENTION

The present invention relates to a lidar system, lidar system components, and associated methodologies for enabling remote identification of aerosol particles. In particular, the invention is directed to the use of a lidar beam to determine at least one characteristic of identified aerosol particles, for example, to distinguish particles having a first chemical composition from particles having a second chemical composition. In this manner, for example, potentially harmful or regulated substances may be distinguished from harmful substances. Such characterization may be based on analysis involving one or more parameters beyond the timing or amount of backscattered radiation, e.g., by analyzing the polarization of the backscattered radiation or detecting induced fluorescence. Preferably, at least part of this functionality is achieved using eye-safe beams.

One embodiment of the invention includes a transmitter that enables transmission of a substantially linearly polarized optical beam that is composed of light in a single polarization plane. Additionally, a receiver and processor capable of quantifying the polarization of light backscattered from aerosol particles is provided, enabling the determination of physical characteristics of the aerosol particles and enabling the comparison of the detected backscatter signature to known signatures in a database to identify the aerosol particles. The detected backscatter radiation can be quantified by calculating a depolarization ratio, which is defined as the ratio of the backscattered light that is polarized in a plane substantially perpendicular to the polarization plane of the transmitted beam to the backscattered light that is polarized in a plane substantially parallel to the polarization plane of the transmitted beam. Therefore a depolarization ratio of zero indicates that all of the backscattered radiation is returned in a plane parallel to the plane of transmission and a depolarization ratio of one indicates that an equal amount of backscatter is detected in each plane. This can be expressed as:

$$\Delta(r) = P_\perp(r)/P_\parallel(r) \quad (1)$$

where r is the range from the system to a point in the atmosphere, $\Delta$ is the depolarization ratio, $P_\perp$ is the perpendicular backscatter intensity, and $P_\parallel$ is the parallel backscatter intensity.

An embodiment of the present invention is capable of rapidly determining a depolarization ratio from the backscattered radiation of a transmitted pulsed beam. One implementation is capable of determining the depolarization ratio of aerosol plumes from a single laser pulse to ranges of several kilometers. This is possible because of the high pulse energy that generates sufficient backscatter signal that it can be distributed across at least two detectors (perpendicular channel and parallel channel) from a single pulse. The backscattered radiation may be integrated over a very short period of time, e.g. a single or small number of pulses, while operating in an eye-safe manner. This enables this embodiment of the present invention to scan significant sections of the atmosphere in a timely manner. This further enables the present embodiment to provide data that can be used to generate a dynamic representation of the polarization attributes of aerosol particles in large sections of the atmosphere. It the context of this invention "remote identification" is used to connote more than simply the determination of the state of a known particle such as whether water vapor is in a liquid or solid form. "Remote identification" is used in the context that an embodiment of the present invention is capable of providing information to help identify unknown aerosol particles by parameterizing and analyzing backscattered radiation. For example, an embodiment of the present invention could be used to determine characteristics of emissions from an industrial site or a plume of suspected chemical or biological agents. "Remote identification" also refers to the ability of the present invention to distinguish between aerosol particle types where the aerosol particle types differ with respect to chemical composition. For example, if two plumes of differing depolarization characteristics were drifting in an area of interest, such as an urban area or battlefield, an embodiment of the present invention could be used to track and distinguish each plume.

The depolarization ratio can be used to remotely identify aerosol particles. When single-plane linearly polarized radiation is reflected by a particle, the polarization components of the backscattered radiation are a function of the shape of the particle. For example, spherical shaped particles will tend to backscatter a greater amount of linearly polarized radiation in a plane parallel to the plane of transmission whereas more complicated particle shapes will produce more linearly polarized backscatter radiation out of the plane of transmission. Therefore, differently shaped particles will produce differing depolarization ratios allowing for identification of the aerosol particles. Other parameters, such as, for example, fluorescence, aerosol scattering, and molecular scattering, may, in combination with the depolarization data, aid in identifying unknown aerosol particles.

An embodiment of the present invention can be also be used to infer phase (liquid, solid or some combination thereof) of a cloud if the cloud particles are known to be water. For example, Cumulus clouds are composed of liquid droplets and Cirrus clouds are composed of ice crystals. Therefore, the present embodiment may be used to infer the phase of the cloud in question. This is, in fact, the traditional application of previous depolarization lidars. However, an embodiment of the present invention extends this technique to atmospheric aerosol clouds. For example, aerosols may be composed of solid, non-spherical particles such as windblown mineral dust or combustion soot. Atmospheric aerosols may also be composed of spherical particles. These tend to be liquid droplets. Liquid droplets can be formed by condensation of water vapor onto hygroscopic nuclei (such as NaCl), gas-to-particle conversions or man-made aerosol generators used to spray solutions onto agricultural fields. An embodiment of the present invention is able to distinguish between spherical and non-spherical aerosol particles as well as between plumes of non-spherical particles with differing depolarization attributes.

The present inventors have recognized that there exists a need for a remote aerosol particle identification system that can safely, quickly and efficiently identify specific types of aerosol particles located in the atmosphere without the need for extraordinary safety precautions, lengthy time-averaging of backscattered radiation to achieve acceptable signal-to-noise ratios, nor the requirement that the transmitted laser be tuned to detect a specific type of aerosol particle. The present inventors have also recognized the need for a remote aerosol particle identification system that can scan the atmosphere at a rate sufficient enough to provide accurate and timely information about the structure and movement of the identified aerosol particles.

Preferably, the system should produce sufficient backscatter energy to support the particle characterization within a reasonably short time window. Therefore the system is preferably capable of identifying the constituents of an aerosol structure from a single or at least a small number of beam pulses. Accordingly, achieving high temporal identification of aerosol particles involves a number of parameters at the component and system levels. Identifying and addressing these issues provides a significant motivation related to the various aspects of the invention as set forth below. Also it is beneficial that the system is capable of operating in an eye-safe mode in that it produces an energy output within the eye-safety standards of American National Standard for the Safe Use of Lasers, ANSI Z136.1-2000, which is incorporated herein by reference.

As previously stated, the present inventors have recognized that it would be useful to remotely identify aerosol particles, e.g., it would be useful to remotely distinguish between benign and potentially harmful aerosol particles in the atmosphere. This remote identification can be accomplished by the analysis of returned radiation from transmitted radiation that interacts with atmospheric aerosol particles to determine aerosol particle parameters such as, for example, particle shape, behavior and chemical composition. The analysis can be comprised of examining such characteristics as polarization, molecular and aerosol scattering, fluorescence, wave properties, and other optical phenomenon. The analysis of the polarization attributes of backscattered radiation to remotely determine atmospheric aerosol particle characteristics described herein is a promising aspect of the broader ability to remotely characterize atmospheric aerosol particles using a transmitted beam of radiation.

In accordance with one aspect of the present invention, a lidar system capable of remote identification of atmospheric aerosol particles is provided where the transmitter is capable of transmitting an optical beam that is substantially linearly polarized and is limited to a single polarization plane. The system also comprises a receiver capable of detecting the backscatter from the transmitted beam and converting the backscatter into electrical signals that form an electrical signature. The electrical signature may include information representing the amount of backscattered radiation with a polarization parallel to the plane of transmission and information representing the amount of backscattered radiation with a polarization perpendicular to the plane of transmission. The system may further comprise a processor capable of determining at least one characteristic of the aerosol particles based on the electrical signature. The system may further comprise a database containing known polarization signatures, which correlate to particular aerosol particles. The acquired signature can then be compared to the database of known signatures to determine the aerosol particle type. The system may be capable of obtaining polarization information from a single eye-safe pulse of the transmitter to ranges of several kilometers.

In accordance with another aspect of the present invention, a lidar system is provided where the transmission of an optical beam having a primary wavelength between about 1.5-1.8 microns is limited to laser light in a single polarization plane. This may be achieved by the use of a thin film plate polarizer in the transmitter that removes components of polarization that are not in the main polarization plane of the beam source. Beam components reflected from the thin film plate polarizer may be directed into a beam dump such as a black box or other optical absorber. The beam dump would be used to safely disperse the energy of the beam components reflected from the thin film plate polarizer. The highly polarized beam can also be directed through a Faraday isolator to prevent back reflections returning to, and possibly damaging, the beam source.

In accordance with another aspect of the present invention, a lidar system is provided where the beam source can be a laser, for example, a Nd:YAG laser pump, transmitting a beam at a source wavelength. After single-plane polarization and prior to transmission into the atmosphere, the beam may be passed through a Raman wavelength shifter to shift the beam wavelength from the source wavelength to the transmission wavelength having a primary wavelength between about 1.5-1.8 microns. The single-plane polarization of the beam facilitates the use of a coating-free Raman cell where all optical surfaces are oriented at the Brewster angle and multiple passes are completed by total internal reflections from interior prisms.

In accordance with another aspect of the present invention, a lidar system is provided comprising a receiver that is comprised of collection optics to collect the backscattered radiation and direct it into a compressed beam and a beam splitter to split the compressed beam into two separate beams perpendicular to each other. The beam splitter may be in a known orientation relative to the transmission polarization; for example, the first beam may be substantially polarized in a plane parallel to the polarization plane of the transmitted beam and the second beam may be substantially polarized in a plane perpendicular to the transmitted beam. Furthermore, each beam is focused onto a separate detector and each detector converts its respective incident polarized beam into an electrical signal representative of its incident beam. The detector may make use of analog direct detection of the backscattered energy to generate the electrical signals.

In one implementation of this aspect, the beam splitter may be a Glan-Taylor Calcite air-spaced beam splitter cube with a single side exit. The beam splitter cube may be oriented so that the beam passing straight through the cube contains light of linear polarization parallel to the polarization plane of the transmitted beam and the beam exiting the side of the cube contains light of linear polarization perpendicular to the polarization plane of the transmitted beam. The beam splitter cube may, for example, have a 25 mm clear aperture and be anti-reflective coated for use at the transmission wavelength.

In another implementation of this aspect, a ½ wave plate can be interposed between the collection optics and the beam splitter. The ½ wave plate may be mounted on a rotary mount to allow the ½ wave plate to be selectably oriented at either 0° or 45° relative to the polarization plane of the transmitted beam. When oriented at 0°, the ½ wave plate has no effect on the beam passing through it. When oriented at 45°, the ½ wave plate converts all of the collected linearly polarized backscatter to circular polarization. The circularly polarized light is then split into two equal beams as it passes through the beam splitter. This equal division of the beam allows the gains of each of the detectors to be matched to enhance system performance.

In accordance with another aspect of the present invention, a lidar system is provided including a receiver which is comprised of collection optics to collect the backscattered radiation, split the compressed beam into two separate beams, and focus each beam onto a separate detector where the field of view of each detector is less than 0.5 mrad and, preferably, less than about 0.2 mrad.

In accordance with another embodiment of the present invention, a lidar system is provided for transmitting a single-plane, linearly polarized optical beam into the atmosphere, receiving the backscatter from the single-plane, linearly polarized optical beam, splitting the received optical beam into components of linearly polarized light parallel and perpendicular to the polarization plane of the transmitted beam and calculating a depolarization ratio.

In accordance with another aspect of the present invention, a lidar system is provided for transmitting a single-plane, linearly polarized optical beam into the atmosphere and receiving the backscatter from the transmitted optical beam. The system includes beam-directing optics capable of scanning the atmosphere in two axes from near ground elevation. In this regard, the system is capable of determining characteristics of atmospheric aerosol particles, including aggregate characteristics such as, for example, plume structure, shape and movement, based on the parameters of the backscattered radiation for a large section of the atmosphere.

In another aspect of the present invention, a lidar system is provided for transmitting an optical beam of known polarization characteristics, receiving a return signal from the transmitted optical beam, and processing the return signal to determine at least one characteristic of the aerosol particles based on the polarization characteristics of the return signal. The system may process the return signal by dividing the return signal into a plurality of separate signals of unique polarization characteristics. The separate signals can then be analyzed to determine at least one characteristic of the aerosol particles. The system may be capable of obtaining range and depolarization information from a single eye-safe pulse of the transmitter. The transmitted beam may have a primary wavelength between about 1.5-1.8 microns.

In accordance with a further aspect of the present invention, a lidar system capable of remotely identifying at least one characteristic of atmospheric aerosol particles from a single or at least to a small number of optical pulses is provided where the optical beam produced by the system is eye-safe in that the total energy transmitted is below the maximum eye-safe energies permitted under American National Standard for the Safe Use of Lasers, ANSI Z136.1-2000. Furthermore, the transmitted beam may have a primary wavelength between about 1.5-1.8 microns. The optical beam may be linearly polarized in a single polarization plane. A receiver and processor capable of determining the ratio of backscattered radiation returned to the receiver in the polarization plane parallel to the polarization plane of the transmitted beam to the backscattered radiation returned to the receiver in the polarization plane perpendicular to the polarization plane of the transmitted beam may also be present. Thus, a lidar system according to this aspect of the invention is capable of determining a depolarization ratio of aerosol particles by transmitting a single or at least a small number of eye-safe beam pulses. The system may include a processor to compare the characteristics of the received backscattered radiation to a database which contains a library of backscattered radiation profiles correlated to known aerosol particles in order to identify aerosol particles in the atmosphere.

In accordance with one aspect of the present invention, a transmitter is provided, for example, for use in an atmospheric aerosol lidar system, capable of transmitting an optical beam that is substantially linearly polarized in a single polarization plane where the primary wavelength of the transmitted beam is between about 1.5 to 1.8 microns. The linear polarization may be achieved by a thin film plate polarizer placed at the output of the optical beam source. Beam components reflected from the thin film plate polarizer can be directed into a beam dump such as a black box or other optical absorber. The highly polarized beam can then be transmitted through a Faraday isolator to prevent back reflections returning to the beam source and damaging it. The transmission wavelength may be achieved by an optical beam source transmitting at a source wavelength and a wavelength shifter to shift the wavelength of the optical beam source to the transmission wavelength between about 1.5 to 1.8 microns.

In one implementation of this aspect, the beam source can be a Nd:YAG laser pump transmitting a beam at a source wavelength. The wavelength shifter may be a Raman wavelength shifter where the polarization of the incoming beam facilitates the use of a coating-free Raman cell where all optical surfaces are oriented at the Brewster angle and multiple passes are completed by total internal reflections from interior prisms. Furthermore, the transmitter may include beam-directing optics capable of scanning the atmosphere in two axes from near ground elevation.

In accordance with another aspect of the present invention, an optical beam receiver for collecting backscattered radiation from a transmitted beam having a primary wavelength between about 1.5-1.8 microns is provided, for example, for use in an atmospheric aerosol lidar system, comprised of collection optics to collect backscattered radiation and direct it into a compressed beam, a beam splitter to split the compressed beam into two separate beams, a first beam which is substantially single-plane linearly polarized and a second beam which is substantially single-plane linearly polarized in a plane perpendicular to the polarization plane of the first beam. In one implementation of this aspect where the transmitted beam is single-plane polarized, the first beam may be oriented so that it is substantially in the plane parallel to the single plane of polarization of the transmitted beam. Furthermore each beam is focused onto a separate detector and each detector converts its respective incident polarized beam into an electrical signal representative of its incident beam. A processor may be included to calculate a depolarization ratio.

In one implementation of this aspect, the beam splitter may be a Glan-Taylor Calcite air-spaced beam splitter cube with a side exit. The beam splitter cube can, for example, have a 25 mm clear aperture and be anti-reflective coated for use at the transmission wavelength.

In another implementation of this aspect, a ½ wave plate can be interposed between the collection optics and the beam splitter. The ½ wave plate may be mounted on a rotary mount to allow the ½ wave plate to be selectably oriented at either 0° or 45° relative to the polarization plane of the transmitted beam. When oriented at 0°, the ½ wave plate has no effect on the beam passing through it. When oriented at 45°, the ½ wave plate converts all of the collected backscatter to circular polarization. The circularly polarized light is then split into two equal beams as it passes through the beam splitter. This equal division of the beam allows the gains of each of the detectors to be matched to enhance system performance.

In accordance with another aspect of the present invention, a receiver is provided which is comprised of collection optics to collect the backscattered radiation, split the compressed beam into two separate beams, and focus each beam onto a separate detector where the field of view of each detector is less than 0.5 mrad and, preferably, less than about 0.2 mrad.

In accordance with a further aspect of the present invention, a methodology is provided for remotely distinguishing between types of atmospheric aerosol particles. The methodology comprises transmitting a beam of radiation of known polarization into an atmosphere, receiving radiation returned as a result of interaction between the transmitted beam and the aerosol particles, then analyzing polarization characteristics of the returned radiation to distinguish between atmospheric aerosol particle types where the particle types differ with respect to chemical composition. For example, the lidar system can distinguish between two or more plumes where each plume is composed of a single or multiple types of aerosol particles where the aggregate depolarization characteristics of each plume are different with respect to every other plume. The lidar system may remotely distinguishing between types of atmospheric aerosol particles from a single or at least to a small number of beam pulses where the total energy transmitted is below the maximum eye-safe energies permitted under American National Standard for the Safe Use of Lasers, ANSI Z136.1-2000. Furthermore, the transmitted beam may have a primary wavelength between about 1.5-1.8 microns. The optical beam may be linearly polarized in a single polarization plane.

In accordance with another aspect of the present invention, a methodology is provided for remotely distinguishing between types of atmospheric aerosol particles. This methodology comprises transmitting a beam of radiation of a first wavelength into an atmosphere, receiving radiation at the first wavelength returned as a result of interaction between the transmitted beam and the aerosol particles, then analyzing the returned radiation to distinguish between atmospheric aerosol particle types where the particle types differ with respect to chemical composition. The lidar system may remotely distinguish between types of atmospheric aerosol particles from a single or at least to a small number of beam pulses where the total energy transmitted is below the maximum eye-safe energies permitted under American National Standard for the Safe Use of Lasers, ANSI Z136.1-2000. Furthermore, the transmitted beam may have a primary wavelength between about 1.5-1.8 microns.

In accordance with a further aspect of the present invention, a methodology is provided for the remote identification of atmospheric aerosol particles. The methodology comprises transmitting a single-plane linearly polarized optical beam, receiving the backscattered radiation from the transmitted optical beam, and analyzing the polarization attributes of said backscattered radiation to identify the aerosol particles. This identification may be with respect to chemical composition. The system may determine a depolarization ratio that can be compared to known ratios to assist in the identification of the aerosol particles. The system may be capable of identifying the aerosol particles from the transmission of a single or very few eye-safe pulses of the optical beam. The transmitted optical pulse may have a primary wavelength between about 1.5 to 1.8 microns.

In accordance with a another aspect of the present invention, a methodology is provided for the processing of backscattered radiation from a single-plane linearly polarized optical beam having a primary wavelength between about 1.5-1.8 microns transmitted into the atmosphere. The methodology comprises receiving the backscattered radiation, collimating the backscattered radiation, splitting the backscattered radiation into two components, a first component that is linearly polarized in a single plane which is in a known orientation with respect to polarization plane of the optical beam and a second component that is linearly polarized in a single plane substantially perpendicular to the polarization plane of the first component, focusing each split beam onto a separate detector capable of providing an electrical signal representative of the incident radiation, and calculating the depolarization ratio. The first component may be oriented so that it is substantially in the plane parallel to the polarization plane of the optical beam. This depolarization ratio may then be compared to depolarization ratios of known substances to identify the aerosol particles.

In accordance with another aspect of the present invention, a lidar system is provided comprised of a transmitter, a receiver and a processor. The transmitter is comprised of a laser pump, which may be a Nd:YAG laser producing a beam having a wavelength of 1064 nm. The output of the laser is passed through a thin film plate polarizer to achieve a high single-plane polarization purity. The beam is then passed through a Faraday isolator to prevent back reflections damaging the laser pump. The beam is next passed through a beam reducer to reduce the diameter of the beam prior to entering a Raman wavelength shifter. The Raman wavelength shifter may be seeded by a seed laser to provide greater beam wavelength control. In this aspect, the Raman wavelength shifter contains recirculating, pressurized methane gas. The beam path is reflected several times within the Raman wavelength shifter and the single-plane polarized 1064 nm beam is converted to an eye-safe single-plane polarized beam with a wavelength of 1543.73 nm via stimulated Raman scattering. The beam exiting the Raman wavelength shifter may have some components that are not at the desired wavelength of 1543.73 nm. These components can be split off by the use of a wavelength dispersive element, such as a Pellin Broca prism, and directed toward a beam dump. The 1543.73 nm beam can then be passed through a beam expander and then to a final mirror oriented to project the beam into the atmosphere.

Still referring to the current aspect, a receiver is included to receive the backscattered radiation as a result of the interaction between the transmitted beam and atmospheric aerosol particles. This receiver may be, for example, a telescope such as a Newtonian telescope or a Schmidt-Cassegrain telescope. The received backscatter is directed through a collimator and interference filter before being directed into a beam splitter. The beam splitter may split the received backscatter into two components: a first component of single-plane linearly polarized light whose polarization plane is parallel to the polarization plane of the transmitted beam and a second component of single-plane linearly polarized light whose polarization plane is perpendicular to the polarization plane of the first component. Each of these components is then directed to a separate detector surface, where the separate detectors each generate an electrical signal representative of their respective detected backscatter. The electrical signals can then be processed to determine a depolarization ratio of the received backscatter. The determined depolarization ratio and characteristics of the electrical signals can be used to identify and/or distinguish types of aerosol particles in the atmosphere. The system may have an attached scanner so that the transmitted beam can be scanned through significant sections of the atmosphere to determine aggregate aerosol particle characteristics such as plume shape and movement.

In accordance with yet another aspect of the present invention, a lidar system employs first and second beams to identify at least one characteristic of aerosol particles. At least one of the beams is eye-safe. For example, an eye-safe lidar beam as described above (e.g., with a primary wavelength between about 1.5-1.8 microns) may be employed to identify an aerosol structure of interest, e.g., a plume in the atmosphere. Thereafter, a second beam may be used to characterize the identified aerosols. For example, the second beam may be employed to induce fluorescence of the particles thereby enabling better characterization. The second beam may or may not be an eye-safe beam. In any event, the use of an eye-safe beam at least for initial aerosol identification allows for use of the system in a broader range of applications and environments, and may provide ranging or other information to assist in aerosol analysis.

Further areas of applicability of the present invention that will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a more complete understanding of the present invention and further advantages thereof, reference is now made to the following Detailed Description taken in conjunction with the accompanying drawings, wherein.

DETAILED DESCRIPTION OF THE INVENTION

In the following description, an embodiment of the invention is set forth first in a high level depiction to describe the basic principles involved in using energy of a known polarization projected into the atmosphere to remotely determine aerosol particle characteristics. An embodiment of the invention is then described in detail in the context of a high pulse energy and Raman shifted Eye-safe Aerosol Lidar (REAL™) system which transmits single-plane linearly polarized energy and divides and separately detects polarized backscattered radiation in the same polarization plane as the transmitted beam and in a plane perpendicular to the polarization plane of the transmitted beam. Indeed, the invention has a number of benefits and provides useful results in this regard. A further embodiment involving multiple beams and selective induced fluorescence is then described. However, it will be appreciated that various aspects of the present invention are not limited to such lidar applications. Accordingly, the following description should be understood as exemplifying the invention and not by way of limitation.

Elastic backscatter lidars are useful tools for atmospheric researchers and commercial users because they are capable of showing the distribution of a plume of aerosol particles in the atmosphere in both space and time. Although the backscatter return from these systems is typically uncalibrated, the images they provide are extremely valuable for identification of boundary layer depth, elevated aerosol layers, wave activity, and sources of pollution. Unfortunately, currently useful atmospheric aerosol lidars are generally not capable of parameterizing physical characteristics of atmospheric aerosol particles beyond aggregate data such as plume position and motion. The ability to determine physical characteristics of the aerosol particles themselves would be of great value in the remote identification of the type of aerosol particle present.

Figure 2:
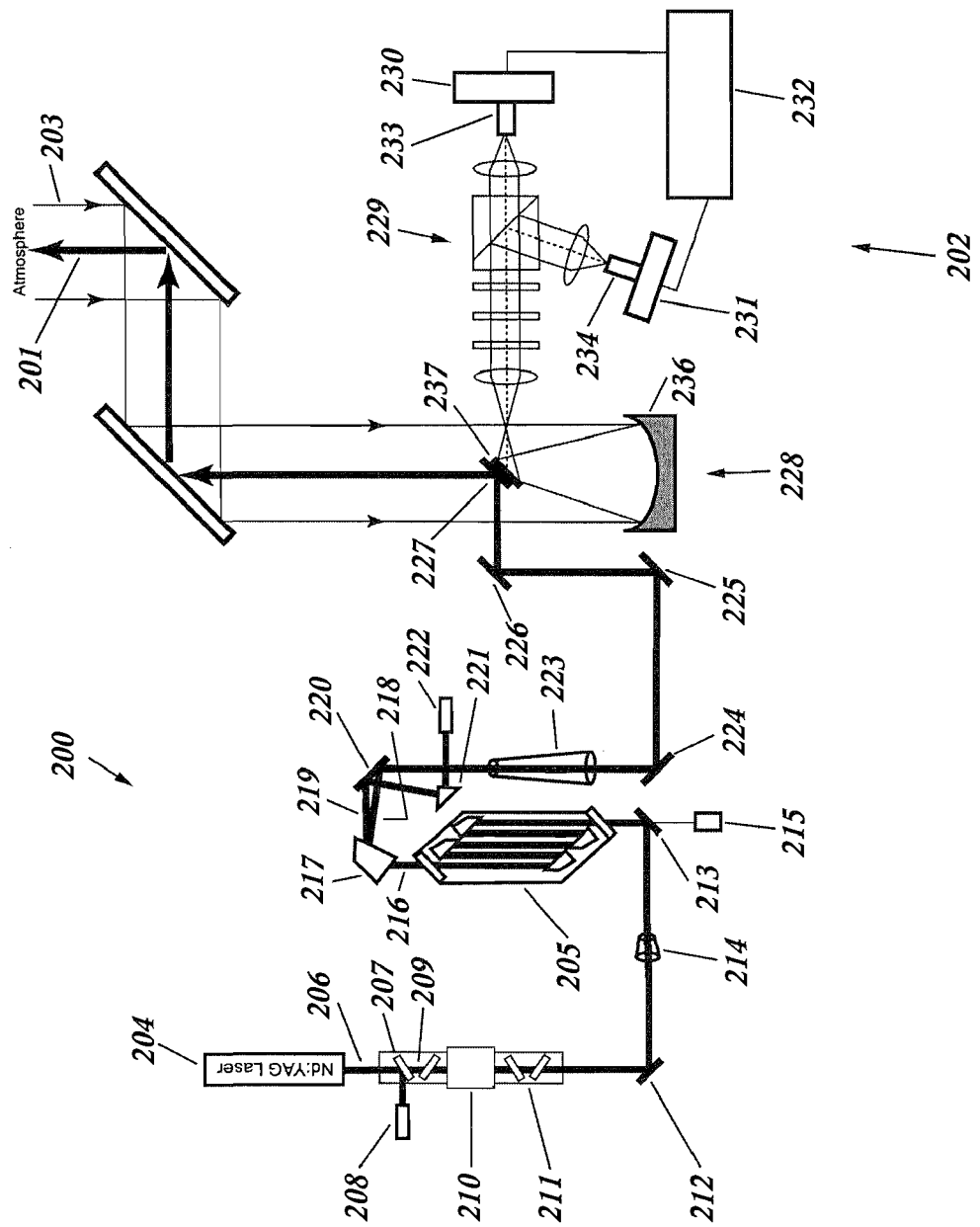
FIG. 2 is a schematic diagram illustrating an alternative embodiment of an atmospheric aerosol particle lidar system in accordance with an embodiment of the present invention.

Current systems of remote identification of atmospheric aerosol particles lack the ability to simultaneously track atmospheric features, such as plume movement, and identify aerosol particle characteristics. This limitation hinders the usefulness of current systems for use in such critical applications as biological or chemical agent detection and tracking where timely plume data and particle identification are critical. Therefore, development of a high temporal scanning backscatter lidar with the ability to identify aerosol particle characteristics is a high priority. Also it is preferable that the system be able to operate in an eye-safe matter. The embodiment illustrated in FIG. 2 is such a system and is discussed below. Also discussed below is how the illustrated embodiment of FIG. 2 achieves maximum pulse energy and therefore minimum detection time while operating in an eye-safe manner.

Figure 1:
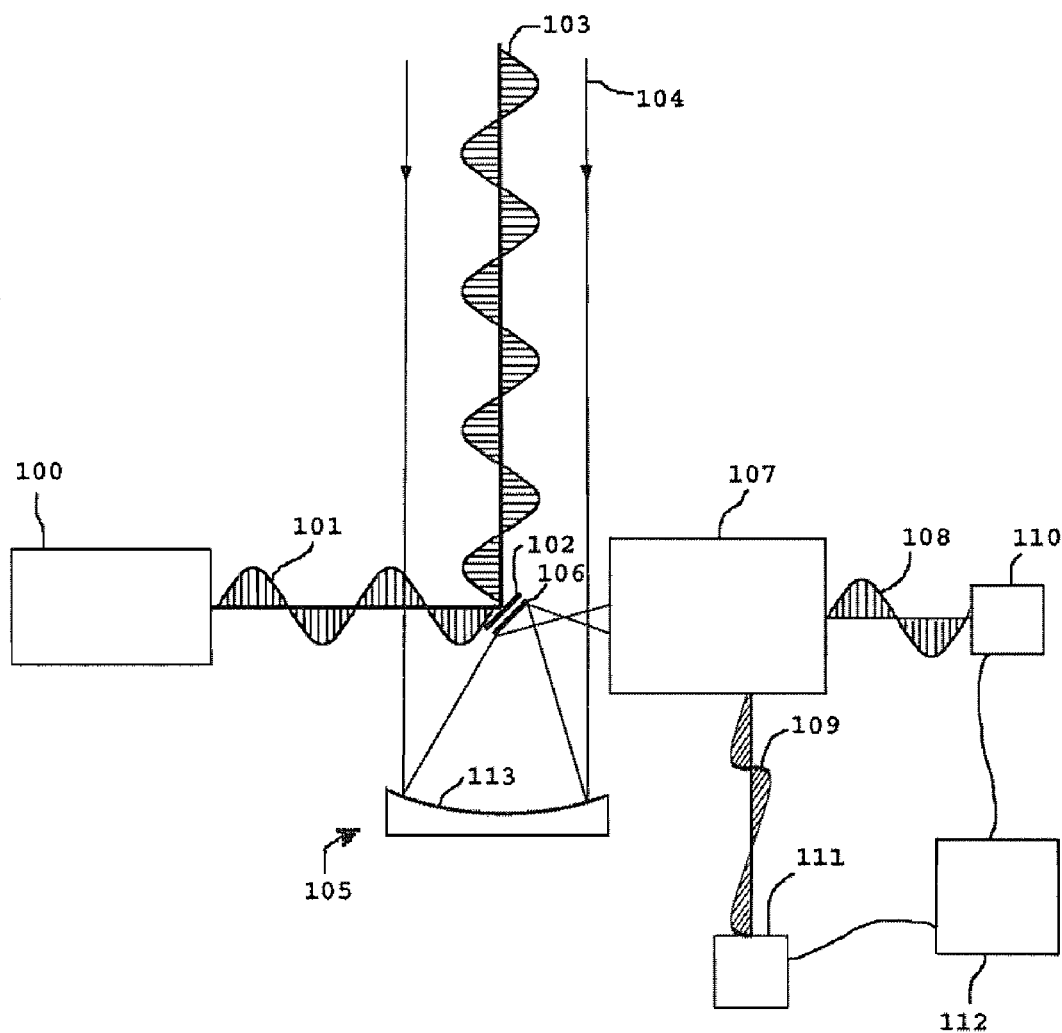
FIG. 1 is a schematic diagram illustrating an atmospheric aerosol particle lidar system transmitting and processing polarized light in accordance with an embodiment of the present invention.

FIG. 1 is a high-level schematic diagram of a system for remotely identifying aerosol particles by transmitting single-plane polarized energy into the atmosphere and determining the polarization characteristics of the backscattered radiation. The system generally includes a beam source 100 of a single-plane linearly polarized beam of energy 101. The beam source 100 must be capable of generating pulsed light of sufficient power so that the amount of backscatter created by the interaction between the beam of energy 101 and the aerosol particles of interest can be detected.

The single-plane polarized beam of energy 101 is generally created by processing a beam from a beam source to achieve the desired intensity, wavelength, and polarization. In FIG. 1, this is represented by the functional block of the beam source 100. The single-plane polarized beam of energy 101 is then directed to a final mirror 102 mounted inside a telescope 105. The final mirror 102 directs the single-plane polarized beam of energy 101 into the atmosphere. The single-plane polarized beam of energy projected into the atmosphere 103 is projected along an axis coaxial with the field of view of the telescope 105.

As the beam of energy 103 propagates through the atmosphere, some of the beam energy will interact with atmospheric aerosol particles and be backscattered along the axis of transmission. This backscattered energy 104 will have polarization characteristics that are at least partially dependent on the type of aerosol particle from which it backscattered. The telescope 105 collects the backscattered energy 104. The system may be utilized in this configuration to obtain vertical images or a scanning system may be disposed in front of the telescope for scanning applications as will be described below. The backscattered energy 104 is reflected off of a primary mirror 113 and a secondary mirror 106 and directed toward beam processing optics 107. In FIG. 1, this is represented by the functional block for the beam processing optics 107.

The beam processing optics 107 splits the backscattered energy 104 into two components: a single-plane linearly polarized beam of energy where the polarization plane is parallel to the plane of transmission 108 and a single-plane linearly polarized beam of energy where the polarization plane is perpendicular to the plane of transmission 109. The parallel beam 108 is then directed to a parallel beam detector 110. The perpendicular beam 109 is directed to a perpendicular beam detector 111.

The detectors 110 and 111 each provide an electrical output signal that is representative of the optical signal intensity incident on their respective detector surfaces. The electrical output signals, which may be amplified, are fed to a digitizer and computer 112. The digitizer and computer 112 then process the output signals from the detectors 110 and 111 and determine characteristics of the aerosol particles based on the polarization characteristics of the backscattered energy 104. This can include the calculation of a depolarization ratio, which is a ratio of the energy detected by the perpendicular beam detector 111 divided by the energy detected by the parallel beam detector 110. Therefore a depolarization ratio of zero would indicate that all of the backscattered energy 104 was returned to the system in the same polarization plane that was transmitted 103. A depolarization ratio of one would indicate that the detectors 110 and 111 each detected an equal amount of backscattered energy.

The backscattered energy 104 that is parallel to the transmitted polarization plane 103 is a result of backscatter due to particles that are spherical in shape. As particles become less spherical, backscattered energy 104 is returned in planes other than the transmitted polarization plane 103. Therefore, a high depolarization ratio data indicates presence of non-spherical particles.

FIG. 2 is a detailed schematic of an embodiment of the invention set forth in the context of a high-pulse energy REAL system constructed in accordance with the present invention. The REAL system generally includes a transmitter 200 for transmitting a low divergence, eye-safe beam 201 into the atmosphere and a receiver 202 for receiving backscattered radiation 203 associated with the transmitted beam 201. The transmitter 200 and receiver 202 are described in turn below.

In the illustrated embodiment, the transmitter 200 includes, among other things, a source pump laser 204 and a Raman cell 205. The combination of a high pulse energy source pump laser 204 and a Raman cell 205 to shift the wavelength of the source beam 206 produces a beam having desired characteristics within the desired wavelength range. In this embodiment, the pump laser 204 is a flash-lamp pulsed, Q-switched, Nd:YAG laser capable of generating 800 mJ/pulse energy at 1064 nm wavelength. Such a pump laser is marketed under the name Continuum Surelite III. The pump laser 204 produces a flat-topped multiple transverse mode beam with pulses of 6 ns full-width half-max (FWHM) in duration. The beam 206 exiting the pump laser 204 is approximately 9 mm in diameter with a divergence of 0.6 mrad.

The source beam 206 is substantially linearly polarized however the source beam 206 does contain significant beam energy not in the desired single plane of transmission. Therefore, the beam 206 is directed to a thin film plate polarizer 207. Beam energy not within the desired single plane of transmission is reflected off of the thin-film plate polarizer 207. Since the beam energy reflected off of the thin film plate polarizer 207 is of a significant amount, it is beneficial to absorb the energy in a controlled manner. In the present embodiment, this is accomplished by directing the reflected energy into a beam dump 208.

The component of the source beam 206 passing through the thin-film plate polarizer 207 is a high-purity single-plane polarized beam 209. The polarization purity of the beam may be on the order of 10,000 to 1. The single-plane polarized beam 209 is then directed through a Faraday isolator 210. The Faraday isolator 210 prevents back reflections from returning to the source pump laser 204, providing optical isolation of the source pump laser 204. The single-plane polarized beam 209 is then passed through an additional thin-film plate polarizer 211 to ensure that the Faraday isolator 210 functions as intended and also to return the single-plane polarized beam 209 to the same axis as the source beam 206.

The single-plane polarized beam 209 is directed to the Raman cell 205 by way of folding mirrors 212 and 213. As will be discussed below, folding mirror 213 has coating properties so as to allow for transmission of a seed beam through the mirror 213 for coaxial alignment of the seed beam and single-plane polarized beam 209.

The Raman cell 205 is a methane Raman cell that operates to convert the single-plane polarized beam 209 having a wavelength of 1064 nm to a first Stokes wavelength of 1.543 microns, which is within the desired range for eye safety. In order to minimize sooting, while providing a beam of sufficient optical density for enhanced wavelength conversion, a beam reducer 214 is employed. The illustrated beam reducer 214 is provided via a small Galilean telescope.

In the illustrated embodiment, the single-plane polarized beam 209 is converted to the eye-safe wavelength via stimulated Raman scattering (SRS) in a pressurized cell filled with pure $CH_4$. SRS is a third-order, nonlinear, inelastic scattering process whereby a sufficiently-high pump field excites molecular vibrations in a medium. The frequency of the scattered light (Stokes output) is shifted by the frequency of these vibrations. Assuming the pump is not depleted, the Stokes intensity as a function of distance is given by the equation $$I_S(z) = I_S(0) e^{g_R I_p z} \quad (2)$$

in which $I_S(0)$ is the initial Stokes intensity, $g_R$ is the steady state Raman gain coefficient, $I_p$ is the pump intensity, and z is the interaction length. The gain coefficient is a function of the Raman active medium and its pressure.

The nth Stokes $\lambda_n^S$, and anti-Stokes, $\lambda_n^{AS}$, wavelengths are given by $$\lambda_n^S = \left( \frac{1}{\lambda_p} - \frac{n}{\lambda_R} \right)^{-1} \text{ and } \lambda_n^{AS} = \left( \frac{1}{\lambda_p} - \frac{n}{\lambda_R} \right)^{-1} \quad (3)$$

respectively, where $\lambda_p$ is the pump wavelength, and $\lambda_R$ is the wavelength of the Raman transition. The wavelength of the Raman active symmetric stretch of $CH_4$ is 3.428 microns. Pumping with 1064 nm results in a 1$^{st}$ Stokes wavelength of 1543 nm, 2$^{nd}$ Stokes wavelength of 2.808 microns and a 1$^{st}$ anti-Stokes wavelength of 0.812 microns. As discussed below, the Raman cell may be designed to suppress the buildup of the 2$^{nd}$ Stokes and 1$^{st}$ anti-Stokes wavelengths.

As seen in Equation 2, the Stokes intensity is a function of pump intensity, pressure of the gas, interaction path length, and the initial Stokes intensity. Typically, the Stokes field is initiated by the spontaneous emission of a photon and therefore the energy and spatial characteristics will fluctuate. To avoid these fluctuations the illustrated cell 205 is seeded with a stable tunable Stokes wavelength laser 215. The illustrated laser 215 may be, for example, a continuous-wave 20 mW telecom diode laser (Mitsubishi FU-68PDF/520M45B). The illustrated laser 215 has a center wavelength of 1543.73 nm and approximately 3 nm tuneability. It is coupled to a single mode, polarization maintaining, fiber which emits a near perfect Gaussian beam. The laser diode driver and associated stable temperature controller (Wavelength Electronics, WLD3343 and WTC3243; respectively) are mounted on a custom circuit board (not shown). The laser 215 can be either current or temperature tuned to match the Stokes emission line. To ease alignment, the diode output is amplified via a 1 W fiber amplifier (IPG Photonics Corp., model EAU-1-C) to 100 mW; however, the additional power provides little to no performance enhancement. The output from the laser fiber is expanded and collimated to match the pump beam diameter, 6 mm, and spatially overlapped by transmitting through the back of the mirror 213, which, in the illustrated implementation, is a gimbal mounted turning mirror. The beam of the illustrated laser 215 is linearly polarized in a single polarization plane. The laser 215 is oriented so that its polarization plane is parallel with the polarization plane of the single-plane polarization beam 209.

The source pump laser beam is reduced in diameter from the 9 mm source beam to a 6 mm diameter beam by beam reduce or 214, which may be in the form of a Galilean telescope. In the present embodiment, the Galilean telescope is composed of two 25.4 mm diameter lenses; one plano-convex and one plano-concave, separated by 12 cm. In particular, the plano-convex lens may be a commercially available lens marketed under the name CVI Part No. PLCX-25.4-180.3-UV-1064 and the plano concave lens may be a commercially available lens marketed under the name CVI Part No. PLCC-25.4-128.8-UV-1064. The resulting beam is substantially collimated rather than focused. That is, the rays of the beam are substantially parallel rather than converging relative to any of the optics of Raman cell 205. It is further noted that the pairing of the folding mirrors 212 and 213 allows for improved circularity of the beam entering the Raman cell 205.

Figure 3:
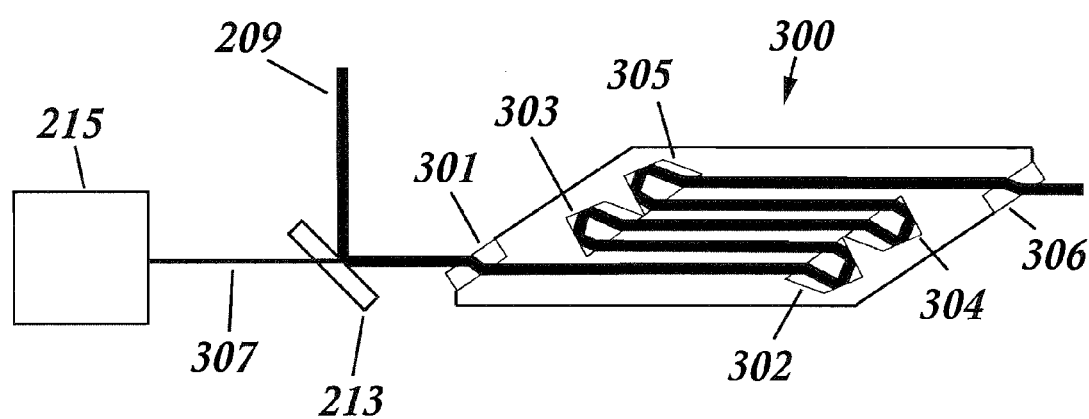
FIG. 3 is a schematic diagram illustrating a Raman wavelength shifter with geometry in accordance with an embodiment of the present invention.

FIG. 3 illustrates an implementation for the Raman cell 300 in accordance with an embodiment of the present invention. The illustrated cell includes an entrance window 301 for allowing transmission of the single-plane polarized beam 209 together with the seed beam 307 from the seed laser 215 into the interior space of the cell 300, internal reflectance elements 302, 303, 304 and 305, and an exit window 306 for allowing transmission of the wavelength shifted beam out of the interior space of the cell 300.

The entrance and exit windows 301 and 306 are oriented at the Brewster angle with respect to the incident beam to eliminate the need for vulnerable AR coatings. The Brewster angle is the angle at which light, in a particular linear polarization state, will pass through an interface without any reflection. The internal reflectance elements 302-305 provide for internal rather than surface reflection of the beams. For example, the elements 302-305 may be prisms. The elements 302-305 thus redirect the light based on total internal reflections thereby eliminating the need for special HR coatings. In addition to having a high damage threshold, the total internal reflection has negligible loss. The elements 302-305 are also oriented at Brewster angles relative to the incident beams to eliminate the need for AR coatings on their front entrance and exit surface. Moreover, the use of the internal reflectance elements 302-305 eliminates beam overlap geometry that would be associated with surface reflecting mirrors. That is, by translating the beam within the elements 302-305 and then maintaining the beams in a parallel relationship within the cell 300, a larger volume of gas is illuminated for higher total gain than compared to a Raman cell with flat mirrors as internal reflectance elements. The windows 301 and 306 and internal reflectance elements 302-305 may be made of, for example, infrared grade fused silica so that they can be used at any wavelength from the ultraviolet to the near infrared. By not incorporating the AR and HR coatings, the illustrated cell 300 can be used at various wavelengths and will be more durable than a cell incorporating the coatings. The higher order Stokes and anti-Stokes lines can be suppressed, e.g., by controlling cell gas pressure and by injection seeding.

Referring again to FIG. 2, the beam 216 exiting the Raman cell 205 generally includes two wavelength components. Specifically, not all of the optical energy is converted from the source laser pump wavelength to the Raman shifted, eye-safe wavelength. It is often desired to transmit only the eye-safe wavelength into the atmosphere. Accordingly, it may be desired to remove the source laser pump wavelength component. In the illustrated embodiment, a wavelength dispersive element 217, such as a Pellin Broca prism, receives the beam 216 and spatially separates the beam 216 into an eye-safe beam 218 and a source wavelength beam 219. The path of the source wavelength beam 219 is folded by mirror 220 and prism 221 to a beam dump component 222. For example, the beam dump component 222 may be a black box or other light absorber.

The eye-safe beam 218 is further processed for transmission into the atmosphere. Specifically, in the illustrated embodiment, the eye-safe beam 218 is processed by a beam expander 223 to impart desired beam characteristics. In this regard, it is desirable to expand the eye-safe beam 218 to provide the desired optical density as well as to improve the beam divergence.

The divergence of a laser beam is given by:

$$\Theta = M^2 \frac{2\lambda}{\pi \omega_o} \quad (4)$$

where $\omega_o$ is the beam waist radius, $\lambda$ is the wavelength, and $M^2$ is defined as the ratio of the beam's divergence to that of a diffraction limited beam of the same waist diameter. Note from Equation 4 that the beam divergence can be reduced by improving the beam quality and/or increasing the beam diameter (beam expansion). The illustrated REAL system capitalizes on this Gaussian beam propagation concept in the transmitter design to reduce the divergence of the transmit beam to fit within the receiver's field of view. First, as noted above, the Raman cell is injection seeded to improve beam quality, and second, the beam is expanded prior to transmitting into the atmosphere.

In the illustrated transmitter, the eye-safe beam 218 is expanded by expander 223, for example, in the form of a Galilean telescope. Specifically, the illustrated expander 223 is a custom lens system including two air-spaced doublets each antireflection coated for the eye-safe wavelength of 1.543 microns (although the coating could optionally be for dual wavelength operation as well). The first 25.4 mm diameter doublet is a negative lens with a focal length of 138 mm. The second 101.6 mm diameter doublet is a positive lens with a focal length of 574 mm. The doublets are separated by 38 cm and expand the beam 4.3 times. The expanded Stokes beam (about 50 mm diameter) has a half angle divergence of 0.20×0.24 mrad. The resulting expanded, low divergence eye-safe beam is transmitted via a folded path into the atmosphere. Specifically, the path of the beam is folded by folding mirrors 224-227, each of which is coated for high reflection at the desired wavelength or wavelengths.

In the illustrated embodiment, the transmitted beam 201 is transmitted on a path that is coaxial with the backscattered radiation 203. It has been determined via ray tracing that such a coaxial transmit/receive configuration desirably achieves full overlap at 500 meters range with small detectors. Such a coaxial configuration is achieved in the illustrated embodiment by transmitting the beam 201 off the back of the telescope secondary. The expanded beam size is therefore preferably limited to the secondary diameter. In this regard, the mirrors 224-227 of the illustrated embodiment are gold-coated 101.6 mm diameter mirrors at 45 degree angles of incidence. Alternatively, dielectric coatings may be used. The edges of the Stokes beam are clipped slightly in this regard. For a 99% transmission of a true Gaussian beam profile, the mirrors 224-227 would need to be 5 mm larger. The final mirror 227, mounted on the back of the telescope secondary, uses electronically controlled motors, marketed under the name New Focus Picomotors to precisely steer the transmit beam to an angle that is within the receiver field of view. Feedback servo-control based on detector readings may be utilized to optimize steering in this regard.

The illustrated receiver 202 generally includes a telescope 228, receiving optics 229, a beam splitter 230, a parallel beam detector 231 for detecting the component of the backscattered radiation 203 that is in a polarization plane parallel to the polarization plane of the transmitted beam 201, a perpendicular beam detector 232 for detecting the component of the backscattered radiation 203 that is in a polarization plane perpendicular to the polarization plane of the transmitted beam 201, a parallel beam signal amplifier 233, a perpendicular beam signal amplifier 234, and a digitizer and computer unit 235. Each of these components is described in turn below.

The telescope 228 includes a primary mirror 236 and a secondary mirror 237. The illustrated telescope 228 is a Newtonian telescope with gold-coated mirror surfaces to provide approximately 90% transmission at 1.5 microns. Another option for the telescope 228 is a 40.6 cm diameter f/10 Schmidt-Cassegrain telescope (Meade LX 200 EMC). The noted Schmidt-Cassegrain telescope with gold-coated surfaces provides a transmission of about 72%. Dielectric coatings may alternatively be used in this regard.

The illustrated telescope 228 is mounted in a fixed vertical position. The system may be utilized in this configuration to obtain vertical images or a scanning system may be disposed in front of the telescope for scanning applications as will be described below. In the illustrated system, the backscattered radiation 203 is collected by the telescope 228 and directed to the receiving optics 229. The receiving optics 229 are illustrated in a FIG. 4.

Figure 4:
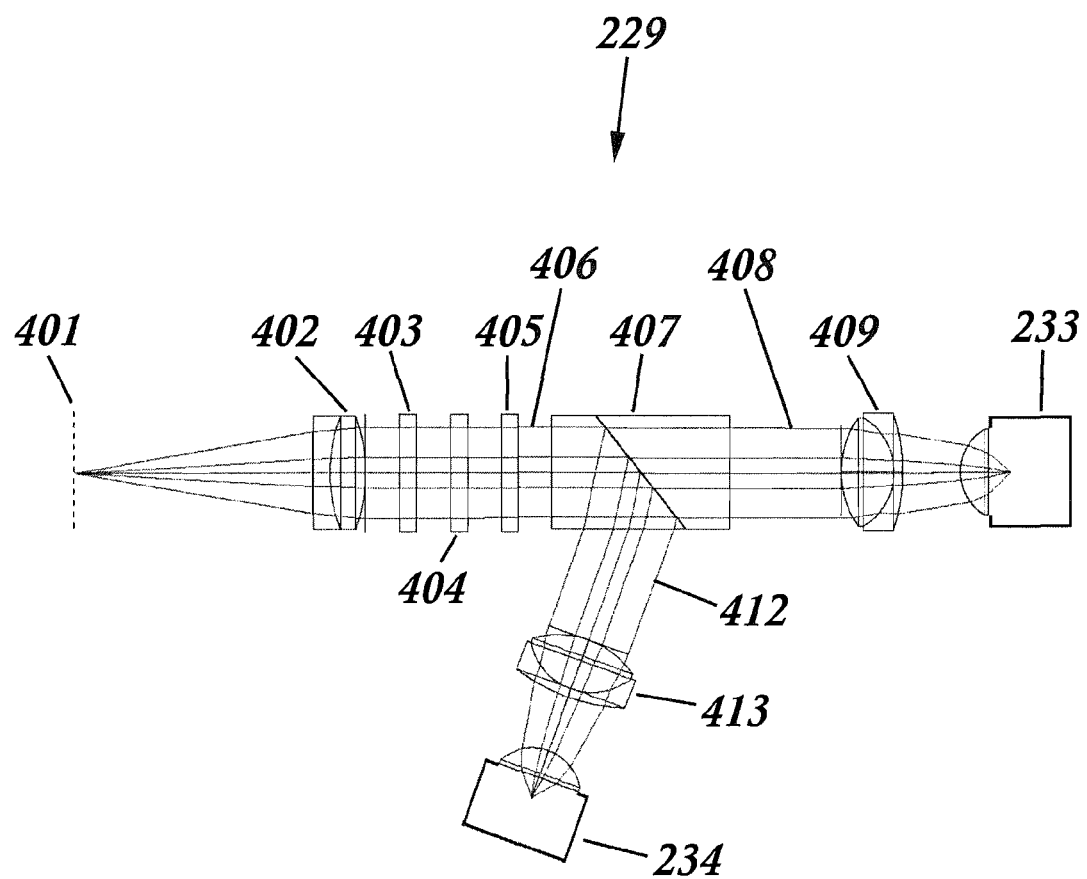
FIG. 4 illustrates a ray trace of the receiver of the system of FIG. 2 from the focal plane of the telescope to the detectors.

Turning to FIG. 4, the received backscattered radiation enters the receiving optics 229 from the focal plane of the telescope 401. The received backscatter is collimated by collimating lens 402 which may be, for example, a 25.4 mm diameter doublet lens. The collimated beam is passed through a neutral density filter 403 that allows the backscatter signal to be attenuated to prevent saturation of the detectors. The illustrated neutral density filter 403 has six settings: 0, 0.5, 1.0, 1.5, 2.0, and 2.5 which correspond to allowed transmissions of 100, 31.6, 10.0, 3.16, 1.0, and 0.316 percent, respectively. The collimated beam facilitates transmission through an interference filter 404. The interference filter 404 provides wavelength-dependent filtering to reject noise that could otherwise compete for the dynamic range of the receiver 202. The illustrated filter 404 is a narrow bandpass interference filter (Omega Optical, Inc. 25.4 mm diameter, 1543.3 nm center wavelength, 5 nm FWHM, with at least 80% transmission).

The illustrated receiving optics 229 further includes a beam splitter 407 to split the collimated and filtered beam 406 into two components. The first beam component 408, which passes straight through the beam splitter 407, contains linearly polarized light in a single plane which is parallel to the polarization plane of the transmitted beam 201. The second beam component 412 contains linearly polarized light in a single plane which is perpendicular to the polarization plane of the transmitted beam 201. All the transmitting, reflecting and processing components in the system must be carefully arranged and oriented to preserve the coordination between the single-plane polarization of the transmitted beam 201 and the parallel single-plane polarization of the first beam component 408. The beam splitter 407, for example, may be a Glan-Taylor Calcite air-spaced polarizer beam-splitter cube with a 25 mm clear aperture. In this embodiment, the Glan-Taylor beam splitter has one side exit and is single layer anti-reflection coated for use at 1543 nm. The illustrated beam splitter was custom fabricated due to the unusually large 25 mm clear aperture by Electro Optical Components Inc.

Along the beam path of the first beam component 408, the illustrated receiving optics 229 further includes a focusing lens 409 for focusing the backscattered radiation in the polarization parallel to the polarization of the transmitted beam 201 onto the active surface of the parallel beam detector 233. The parallel beam detector 233 includes a high gain medium for detection of 1.5 micron wavelength backscattered radiation. A preferred detector for this application is an InGaAs detector. In the illustrated embodiment, the detector is a 200 micron diameter InGaAs/InP avalanche photodiode (Perkins Elmer/EG & G Model No. C30662) with 75% quantum efficiency, a maximum useable gain of approximately 20 and a bandwidth of 200 MHz. More preferably, a detector amplifier unit may be utilized (Perkins Elmer/EG&G Model No. C30659-1550-R2A).

This detector drives the design of the focusing lens 409. The illustrated lens 409 is a three-element design, a doublet with companion meniscus lens, with an 18 mm focal length and 12.4 mm diameter. The lens is designed to collect all light within a 0.15 mrad FOV onto the detector for the range 500 m to 15 km. In practice, the useful range of the instrument is slightly adjustable, analogous to the depth of field of a camera. For example, by moving the position of the detector with respect to the effective focal point of the receiver, the full overlap region can be shifted in either direction. The detector 233, in a shielded enclosure, is mounted on a high precision 3-axis translation stage (Newport ULTRA Line 561D xyz), not shown, for adjustment.

An arrangement similar to the focusing lens 409 and detector 233 along the beam path of the first beam component 408 is located along the beam path of the second beam component 412. As with the equipment along the beam path of the first beam component 408, there is located along the beam path of the second beam component 412 a focusing lens 413 similar to focusing lens 409 and a perpendicular beam detector 234 similar to parallel beam detector 233. In the illustrated embodiment, the focusing lenses 409, 413, beam detectors 233, 234, and amplifiers 230, 231 along each beam path 408, 412 are of the same configuration and components.

For each detector 233, 234, the half angle FOV can be given as the photodetector radius divided by the focal length of the receiver system. In one implementation, the effective focal length of the receiver (telescope and custom optics) was calculated to be 367 mm at 1.543 microns. Therefore the receiver FOV, with a 200 micron diameter detector, is 0.27 mrad (half angle). This receiver FOV is slightly larger than the divergence of the transmitted beam 201, which, in the present illustrated embodiment, is about 0.20×0.24 mrad.

The illustrated embodiment of FIG. 4 additionally discloses a ½ wave plate 405 in a rotary mount located between the interference filter 404 and the beam splitter 407. The rotary mount allows the ½ wave plate 405 to be oriented in one of two positions. In the first position, the ½ wave plate 405 is oriented at 0° and has no effect on the collimated beam 406 passing through it. In the second position, the ½ wave plate 405 is oriented at 45°. In this position the ½ wave plate 405 converts all of the collimated backscatter radiation to circular polarization. The effect of the beam splitter 407 on the circularly polarized light is to split the beam 50-50. Since in this configuration each of the detectors 233, 234 would receive one half of the total backscattered radiation, this configuration allows for the gains of the two detector channels to be matched.

Returning to FIG. 2, the parallel beam detector 233 provides an electrical output signal that is representative of the optical signal intensity incident on the parallel beam detector surface. This output signal is then amplified by parallel beam amplifier 230. In the illustrated embodiment, the amplifier 230 is an operational amplifier (Analog Devices Model ADA29) that has a bandwidth of 55 MHz at a gain of 20. The op amp, photodiode, and power supply are mounted on a custom circuit board in an RF shielded case. In order to amplify return signals that are near the noise level of the detector 233 the noted amplifier 230 is operated with a gain of approximately 850. Unfortunately, this reduces the bandwidth to approximately 1 MHz (350 ns rise time). Operated in this manner, the bandwidth of the amplifier becomes the limiting factor with regard to range resolution. Range resolution can be enhanced in this regard by providing a second stage amplifier.

Similarly, the perpendicular beam detector 234 provides an electrical output signal that is representative of the optical signal intensity incident on the perpendicular beam detector surface. This output signal is then amplified by perpendicular beam amplifier 231. In the illustrated embodiment, the amplifier 231 is also an operational amplifier (Analog Devices Model ADA29) that has a bandwidth of 55 MHz at a gain of 20. As with the parallel channel, range resolution can be enhanced by providing a second stage amplifier.

The noted two-stage amplifiers allow for realization of potential range resolution on the order of 3 m or better. The lidar system of this embodiment of the present invention also yields a signal-to-noise ratio of greater than 10 (taking into account the detector noise, background noise from sky radiance and background noise from molecular scattering) at a distance of 15 km for a single laser pulse (or integration time of less than 0.1 seconds) when pointing at an elevation of less than 5° through low altitude haze.

The analog outputs of the amplifiers 230, 231 are converted to digital signals by at least one analog-to-digital card (GAGE Model 14100) in the digitizer and computer 232, which may be, for example, a personal computer. Each digitizer card is capable of 14 bit quantization. Each is also capable of recording one channel at 100 megasamples per second (MSPS) or two channels at 50 MSPS. Programs may be provided in Labview to display the total backscatter data in real-time and write files to the hard disk. Programs may also be provided in the Labview to display the backscatter data for both the incident radiation detected in a single plane of polarization parallel to the transmitted beam and the incident radiation detected in a single plane of polarization perpendicular to the transmitted beam. In addition to acquiring backscatter data for each polarization orientation, the Labview program is capable of simultaneously monitoring laser energy's location and the temperature and pressure inside the Raman cell via the serial connections. The Labview programs can thereby provide total backscatter images and backscatter depolarization ratio images. In addition, such programs can provide for integration of images over a scanning range of interest to provide integrated volume imaging containing both total backscatter and backscatter depolarization ratio components.

Figure 5:
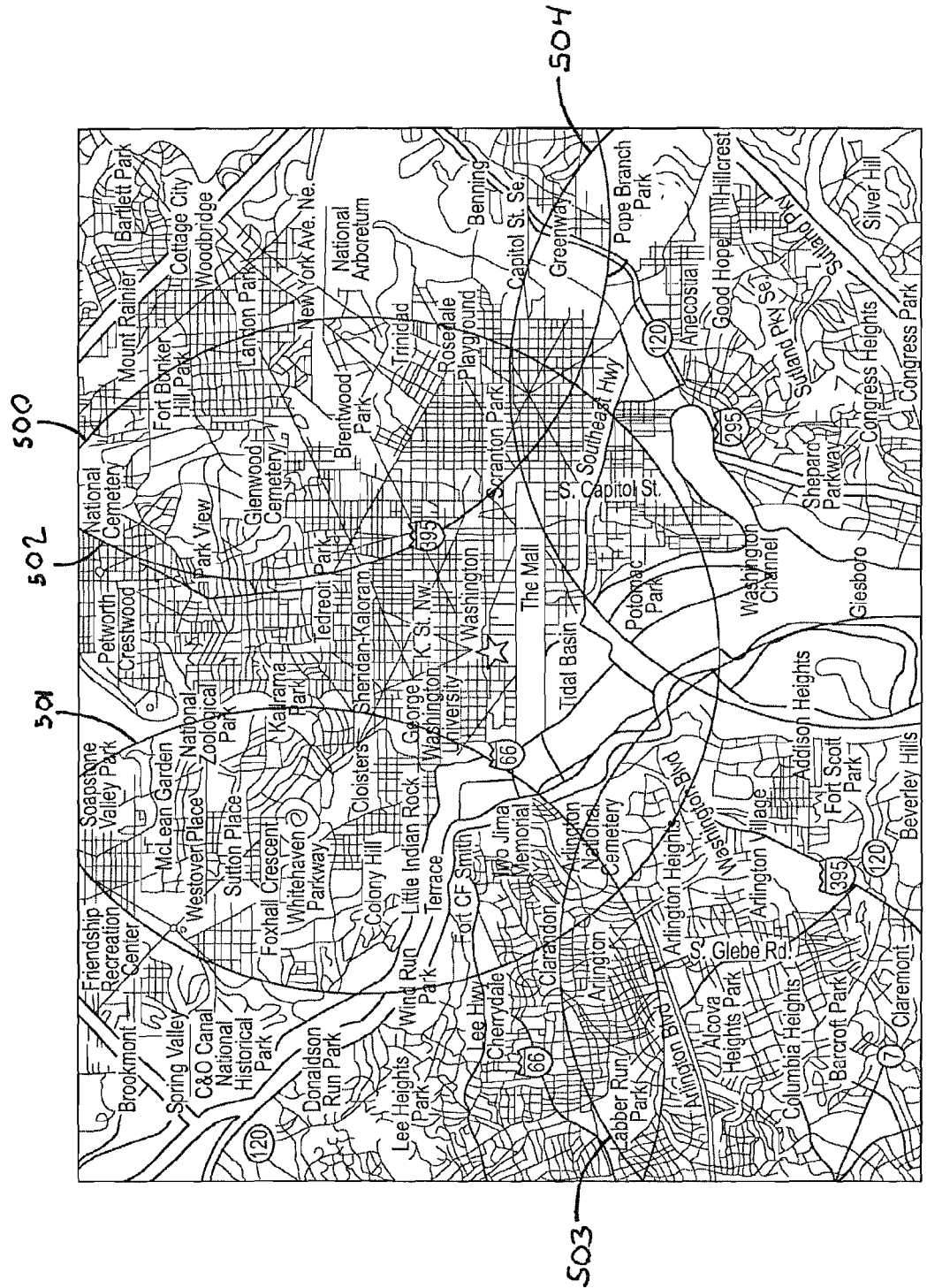
FIG. 5 is a schematic diagram illustrating a network of scanning lidar systems in accordance with an embodiment of the present invention.

As discussed above, it may be desired to scan the transmitted beam across an angular range relative to one or more scan axes. Such scanning capability may be desirable, for example, in connection with operating a network of lidars to identify and monitor aerosols in the atmosphere over a metropolitan area. Such identification and monitoring may be conducted, for example, to determine and monitor sources of pollution or to identify and track the source of harmful agents in the atmosphere. Such a network is schematically illustrated in FIG. 5. Specifically, FIG. 5 illustrates a number of overlapping coverage areas 500-504, schematically illustrated as circles. It will be appreciated that the effective range of each lidar system will vary depending on a number of factors and there is not, in reality, a well-defined edge to any coverage area. However, the various components of the lidar system may be tuned to a desired coverage range. As shown in FIG. 5, the coverage areas may be overlapped to ensure that there are no gaps in coverage or to provide coverage via multiple lidar systems for areas of particular interest. Where adjacent lidar coverage areas overlap, the scanning phase of such neighboring lidar systems may be controlled to provide more frequent coverage in the area of overlap. The network of FIG. 5 corresponds to individual lidar systems that scan a full circular range relative to a vertical axis. Such scanning may be continuous. The lidar systems may also scan across a desired elevation range. In this regard, the scanning relative to the azimuth and elevation axes may be conducted in a raster pattern. The elevation scanning may extend over a 90-degree range so as to define spherical coverage regions associated with each lidar system.

Figure 6:
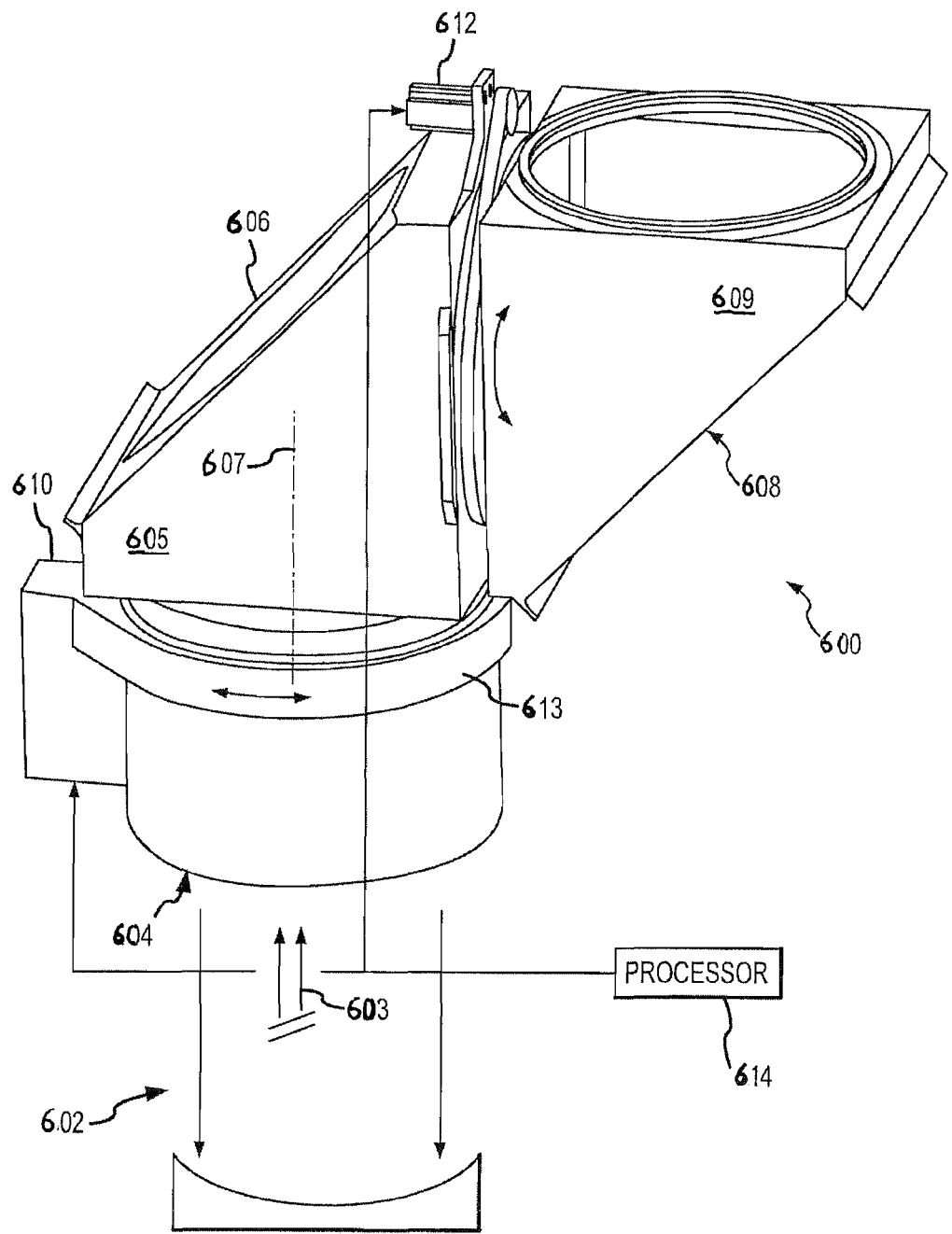
FIG. 6 is a schematic diagram illustrating a scanning system that may be used in connection with the lidar systems of FIG. 1 or FIG. 2.

FIG. 6 illustrates a scanning system 600 for accomplishing such scanning. The scanning system is disposed in front of the telescope 602 of a lidar system. Specifically, a transmitted beam 603 enters the scanning system 600 through an entrance window 604 and is reflected by a first mirror 606 mounted in a first housing section 605 that is rotatable about the telescope optical axis 607. The transmitted beam 603 is redirected by the mirror 606 to a second mirror 608 mounted in a second housing section 609 that is rotatable with respect to the first housing section 605 about an optical axis connecting the mirrors 606 and 608. The combined action of the two mirrors 606 and 608 allows for directing the beam 603 to any desired elevation angle and azimuth angle. The returning backscatter radiation is routed to the telescope 602 by the reverse pathway. It will be appreciated that the mirrors 606 and 608 are movable in a coordinated fashion to direct the transmitted beam and backscatter radiation in this regard. Specifically, a pair of movable mirrors 606 and 608 are used in this regard for enhanced beam circularity and optical efficiency. Moreover, because each mirror 606 or 608 is at a fixed angle relative to the incident beams, the beam footprint on the mirrors does not change and is minimized relative to the full range of scanning angles. The mirrors are driven across the desired range of angular motion by respective azimuth and elevation motors 610 and 612. These motors may be driven by drive signals from the processor 614. The corresponding elevation and azimuth values are recorded by software running on the processor 614 for compiling and recording imaging information.

The illustrated system 600 accommodates continuous 360° azimuth scanning. In this regard, the first housing section 605 may be mounted on a slip ring mounting 613. Because of the coaxial geometry of the lidar system, a single scanning system 600 can be utilized for transmission and reception. Moreover, the illustrated system 600 allows for beam scanning without moving the transmitter and receiver components for improved efficiency and robustness.

As discussed above, the embodiment illustrated in FIG. 2 operates in an eye-safe manner. Operating in an eye-safe manner, as opposed to operating in a non-eye-safe manner, eliminates the requirement that the intended path of a transmitted beam be clear of personnel or objects that could be harmed by a non-eye-safe beam. This enables the use of the system in urban and populated areas and allows for autonomous and continuous operation.

Figure 7:
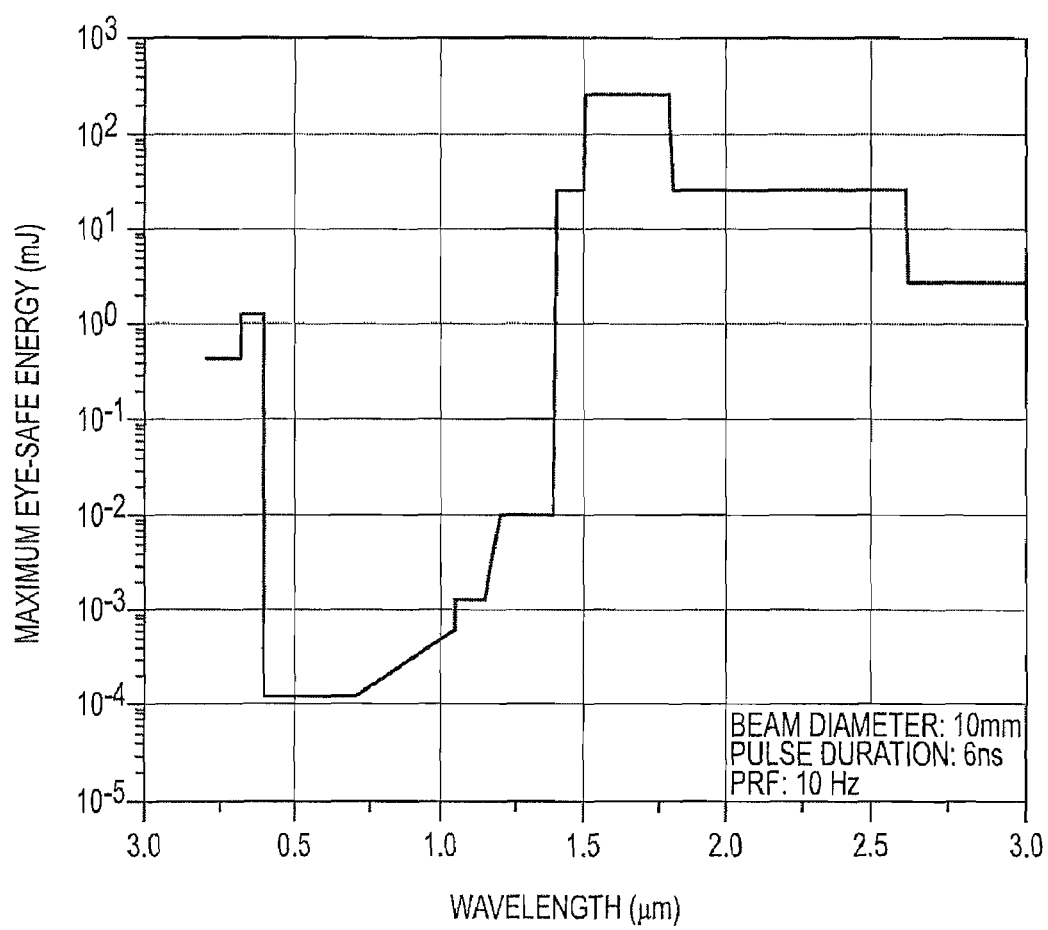
FIG. 7 illustrates the maximum eye-safe energy for a pulse laser according to ANSI standards for particular pulse beam parameters.

There are currently several general approaches for developing an eye-safe lidar. The three broad practical possibilities are: (1) operating at wavelengths less than 0.4 microns, (2) using the micro-pulse technique in the visible part of the spectrum, and (3) operating at wavelengths greater than 1.4 microns. The human eye is particularly vulnerable to wavelengths between 0.4 microns and 1.4 microns because those wavelengths easily pass through the cornea and lens and are focused on the retina. Light at wavelengths less than 0.4 microns and greater than 1.4 microns are safely absorbed in the lens and cornea at the energy densities sufficient for lidar applications. FIG. 7 shows the maximum eye-safe energy ($MPE^2$ times the beam area) for a pulsed laser as a function of beam wavelength permitted under American National Standard for the Safe Use of Lasers, ANSI Z136.1-2000. The chart shows that the region between 1.5 and 1.8 microns has the highest permissible energy. With modest beam expansion it is possible to safely transmit over 1 J per pulse in this region.

The maximum eye-safe energy remains modestly high (similar to 355 nm) for wavelengths longer than 1.4 microns; however, photodetector performance decreases with increasing wavelength. Although Doppler lidars at 2 and 10 microns are successful by using a heterodyne detection method, direct detection lidar in the IR is best performed at 1.5 µm due to the availability of inexpensive, high quantum efficiency detectors which do not require cooling. In addition to these factors, work at infrared wavelengths has the advantage over the ultraviolet in that it features low molecular scattering. Backscattering from molecules in undesirable for aerosol lidars because it reduces the contrast between aerosol backscattering and the noise background. The 1.5 micron wavelength region also features lower sky radiance than a broad range of ultra-violet and visible wavelengths thus improving signal-to-noise ration. When compared to visible region, infrared beams are invisible and therefore eliminate the potential of flash blinding pilots or drawing unwanted attention from the public. Lastly, working in this wavelength allows one to take advantage of recent advancements in the telecommunications sector (e.g., detectors, optical coatings, lasers, etc).

There are a few choices for generating pulsed light in the 1.5 micron wavelength region. The embodiment illustrated in FIG. 2 employs stimulated Raman scattering (SRS) for several reasons including robustness of technique, the quality of the resulting beams including low divergence at the desired power for direct-detection lidar and cost effectiveness.

Figure 8:
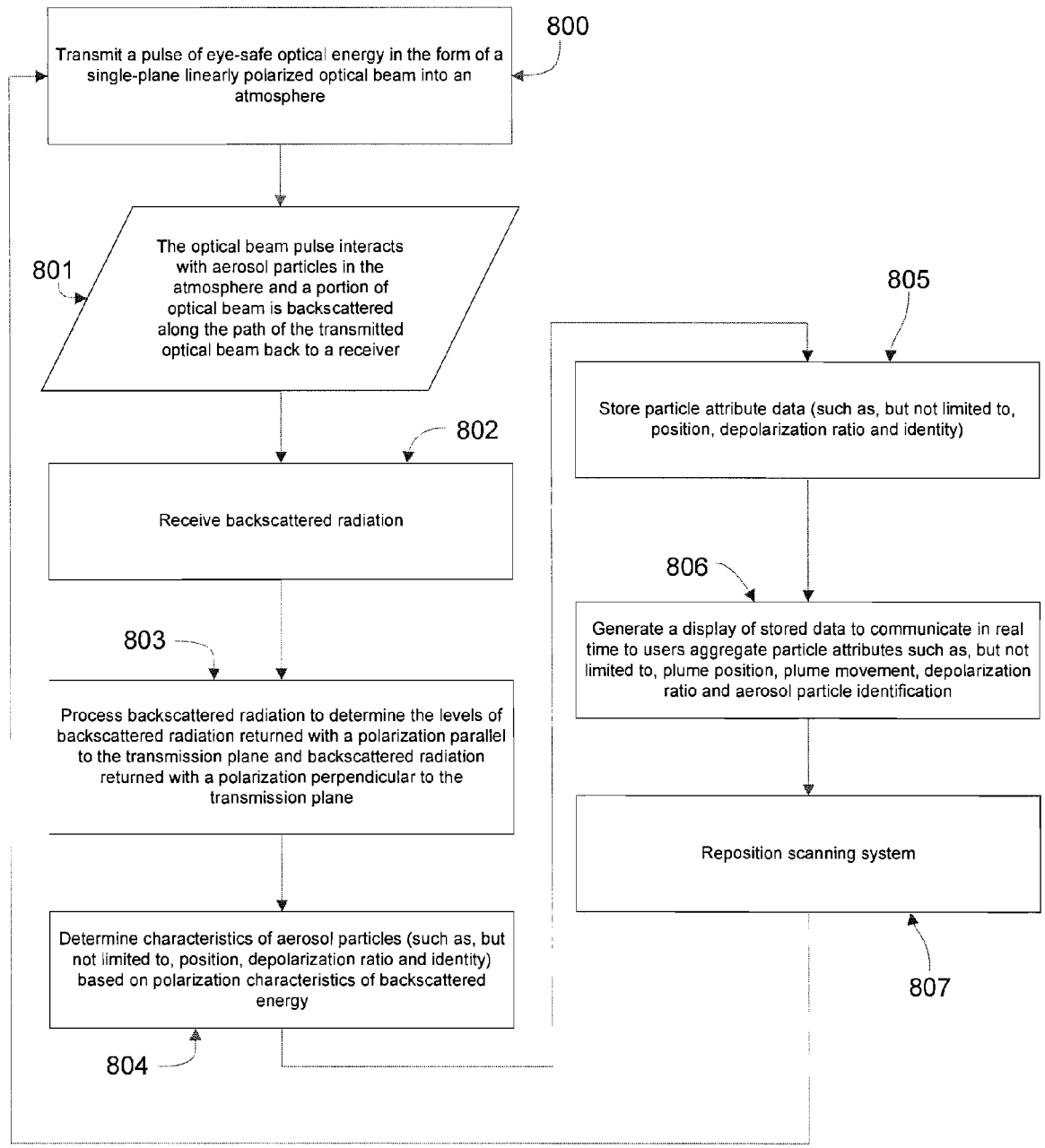
FIG. 8 is a flowchart for a method of remotely identifying aerosol particles in accordance with an embodiment of the present invention.

FIG. 8 illustrates a methodology of remotely identifying aerosol particles in an alternative implementation of the present invention. The illustration is in the form of a flowchart wherein the first step is to transmit 800 an eye-safe pulse of optical energy in the form of a single-plane linearly polarized optical beam into an atmosphere. To maximize eye-safe transmission energy the beam pulse may have a primary wavelength between about 1.5-1.8 microns. Next, the transmitted optical beam travels into the atmosphere and interacts 801 with aerosol particles. As a result of this interaction some of the radiation is backscattered along the path of transmission toward a receiver. Some of this backscattered radiation will be in a plane perpendicular to the polarization plane of the transmitted beam. The amount of this depolarization is dependent on the aerosol particle characteristics.

The next step is to receive 802 the backscattered radiation. The following step is to process 803 the backscattered radiation to determine the amount of depolarization by comparing the amount of backscattered radiation returned with a polarization parallel to the transmission plane to the amount of backscattered radiation returned with a polarization perpendicular to the transmission plane. A depolarization ratio can also be calculated. This process may include such steps as collimating the backscattered radiation and splitting the backscattered radiation into planes parallel and perpendicular to the beam transmission plane of step 800. Processing 803 the backscattered radiation may also include directing and focusing the backscattered radiation on to at least one detector to convert the backscattered radiation into electrical signals. The return polarization attributes can then be used to determine 804 characteristics of the aerosol particles. These characteristics can include, but are not limited to, aerosol particle position, depolarization ratio and identity. Determining 804 characteristics of the aerosol particles may also include comparing the return polarization attributes to a database correlating particular polarization attributes to particular aerosol particles.

The next step is to store 805 the characteristics determined in the previous steps 803 and 804. Then the stored information of step 805 can be used to generate 806 a display of the stored data. This display can be in graphical format and can communicate aggregate aerosol particle characteristics such as, but not limited to, aerosol particle plume position, aerosol particle plume movement, depolarization ratio as a function of position in the atmosphere, and aerosol particle identification.

The next step is to reposition 807 an attached scanning system so that the entire process can be repeated looking at a different section of the atmosphere than the previous cycle. It should be noted that the step of repositioning 807 of the scanning system can also be performed at any step after receiving 802 the backscattered radiation but before the next pulse transmission 800.

Field Test Experiments of Polarization Lidar System

A polarization lidar system according to the concepts and embodiments of the present invention was used to detect atmospheric plumes in a test range setting. The shape of particles hosting bacteria or viruses tends to be either droplets (spheres) or crystals depending on the aerosol generation method used. The experiment was conducted to test the system's ability to detect and discriminate plumes emanating from these different types of aerosol generation methods. During the experiment, the system was tasked with detecting the depolarization characteristics of various plumes released at various ranges in the test range.

The system used was additionally capable of detecting total backscatter intensity. The total backscatter intensity readings were used to verify the location of aerosol particle plumes. The polarization lidar system was then enabled and the depolarization characteristics of various plumes were detected. This was accomplished by having the polarization lidar system scan horizontally across plumes over the test range. Releases of biological aerosol simulants and other particulate plumes were conducted at night to avoid the rapid dispersion caused by more turbulent daytime boundary layers. For each case presented in FIGS. 9, 10, and 11, an image of the total backscatter intensity is shown in part A of the figure and the detected backscatter depolarization ratio is shown in part B of the figure. The backscatter depolarization ratio was computed by dividing the perpendicular channel raw signal by the parallel channel raw signal.

Figure 9A:
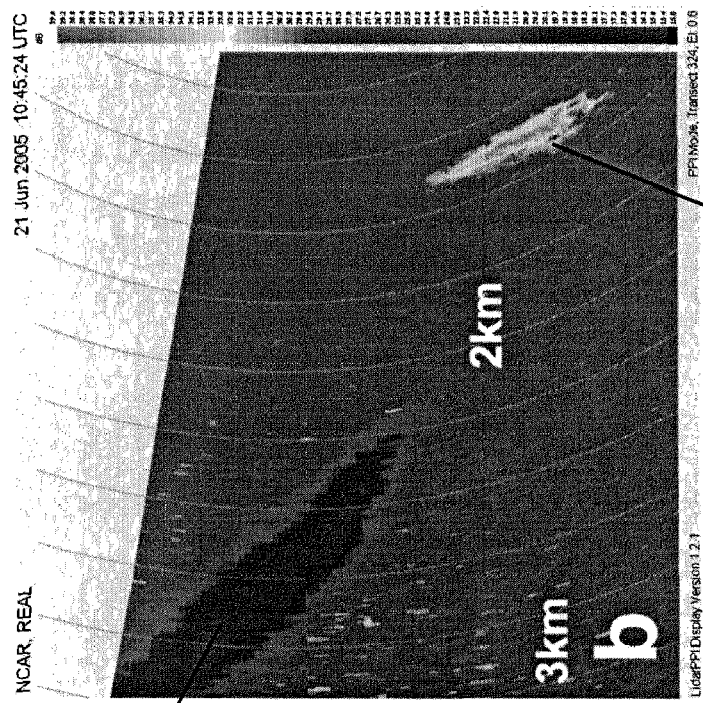
FIGS. 9A-11B show examples of detected backscatter intensity and polarization ratio using a system according to the present invention.

FIG. 9A shows the total backscatter intensity of two separate plumes located between about one and three kilometers away from the system. In the figure, the concentric circles, such as circle 901, represent equidistant lines from the lidar source. For example, circle 902 represents a line of points that are approximately two kilometers from the lidar source. Feature 903 represents the detection of a plume of white smoke from a point release in the test range. Feature 904 represents the detection of a plume of road dust over the test range.

Figure 9B:
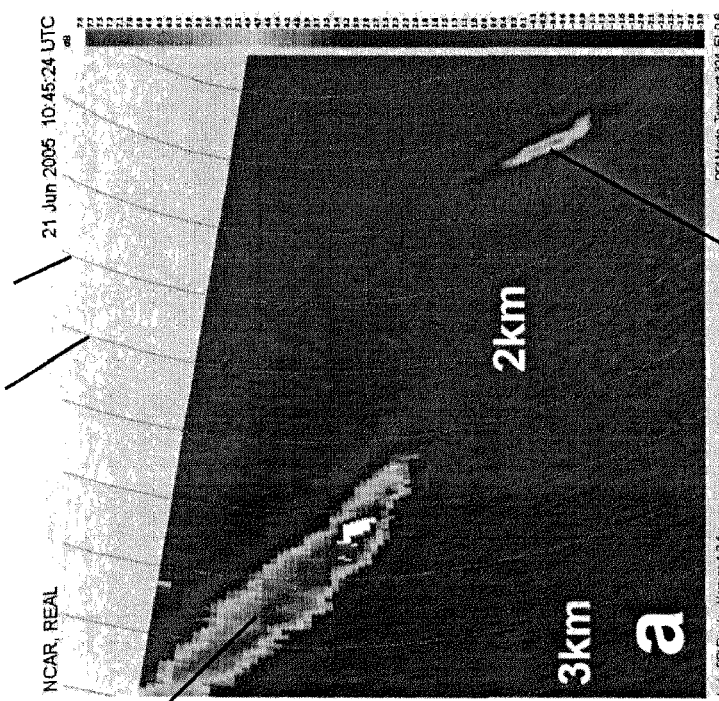

FIG. 9B shows the results of detecting the same atmospheric features as in FIG. 9A with an embodiment of the present invention. Feature 905 is a result of detecting the same plume depicted by feature 903 in FIG. 9A. However, feature 905 depicts depolarization ratio, not the total backscatter intensity. The relatively darker color of feature 905, as compared to the background of the image in FIG. 9B, indicates that the white smoke had a lower depolarization ratio then the background. Feature 906 is a result of detecting the same plume as was labeled 904 in FIG. 9A. The relatively lighter color of feature 906, as compared to the background of the image, indicates that the road dust had a higher depolarization ratio than the background.

The experiment results depicted in FIGS. 9A and 9B confirmed that the depolarization ratio varies according to aerosol type and not some other variable such as concentration or range. These results show a more distant aerosol cloud with substantially lower depolarization than the background aerosol while a closer cloud exhibits higher depolarization. Instrumental systematic errors could not cause this result.

Figure 10A:
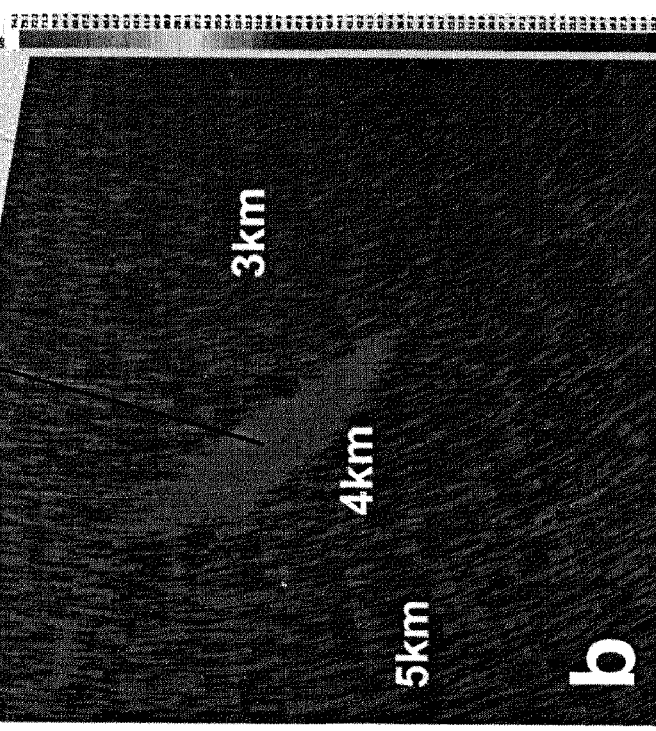
Figure 10B:
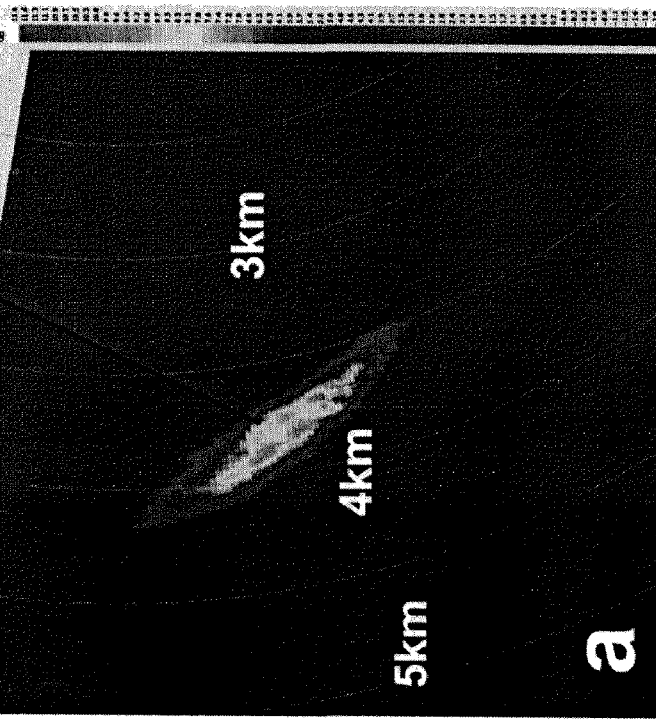

FIG. 10A shows the total backscatter intensity of another plume, different than that depicted in FIGS. 9A and 9B, located between about three and five kilometers away from the system. Feature 1001 represents the detection of a plume of *Bacillus subtilis* var. *niger* (BG) released from an aircraft over the test range. FIG. 10B shows the results of detecting the same atmospheric feature as detected in FIG. 10A with an embodiment of the present invention. Feature 1002 is a result of detecting the same plume depicted by feature 1001 in FIG. 10A. However, feature 1002 depicts depolarization ratio, not the total backscatter intensity. The relatively lighter color of feature 1002, as compared to the background of the image, indicates that the BG had a higher depolarization ratio than the background.

Figure 11B:
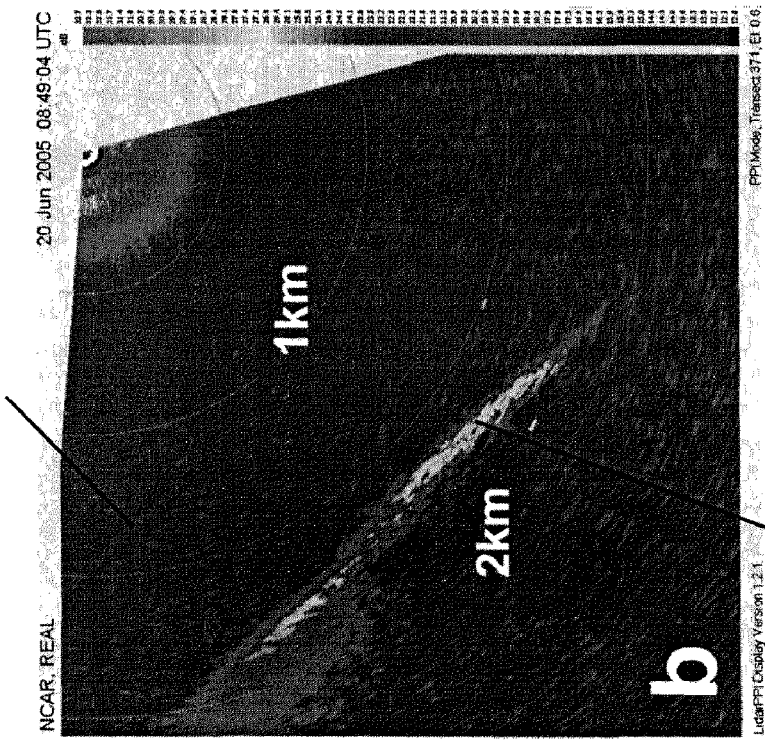
Figure 11A:
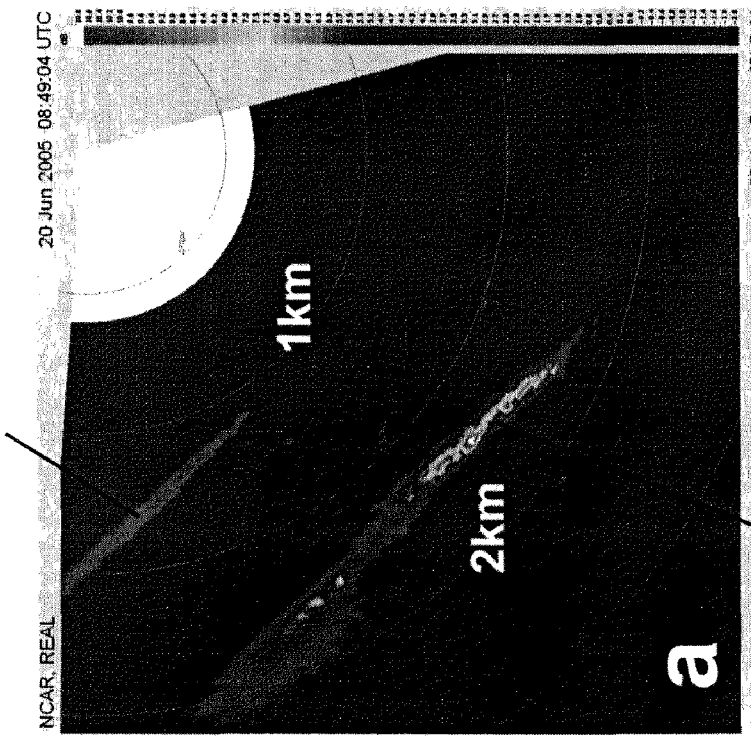
Figure 12A:
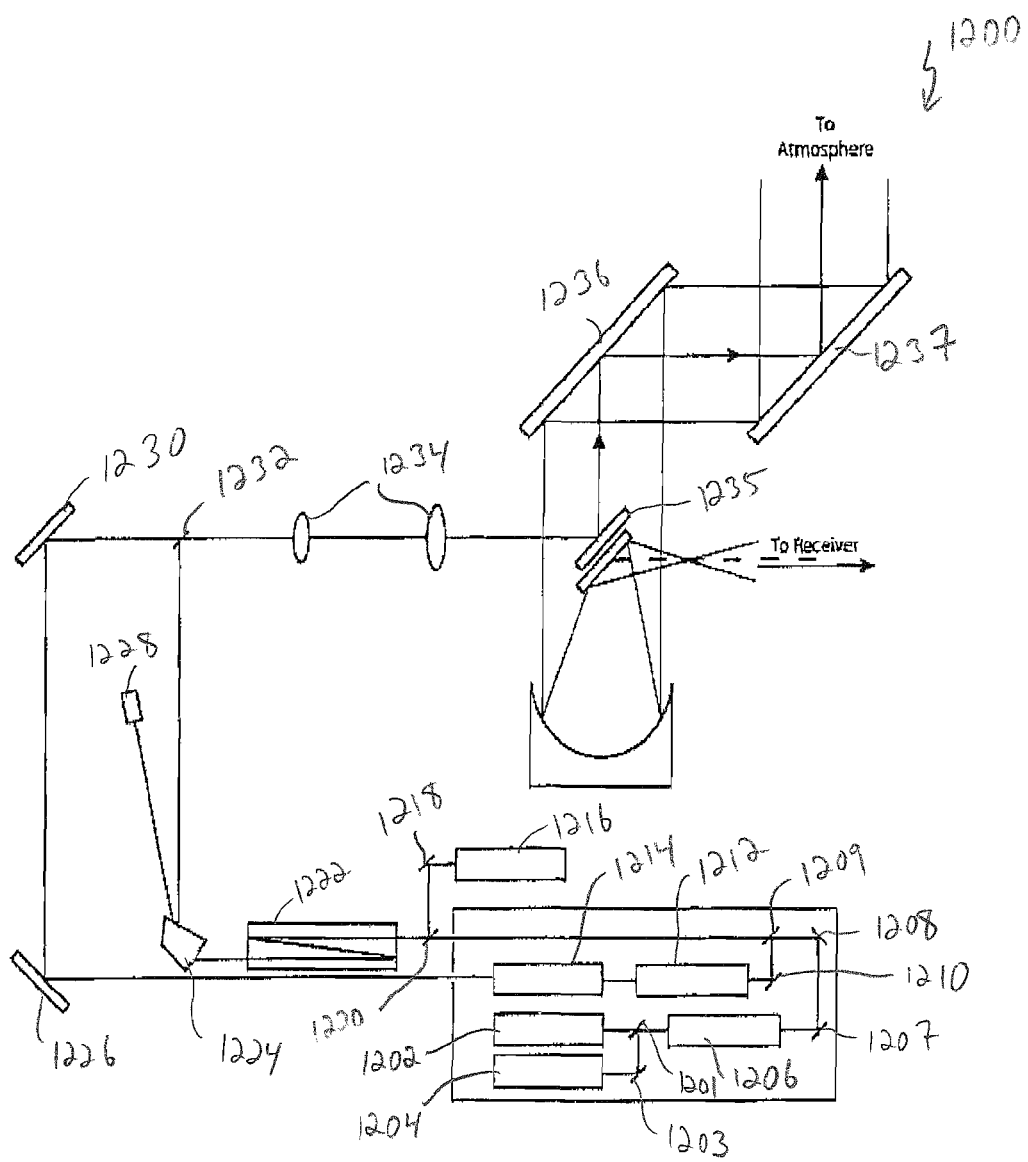
FIGS. 12A-12B illustrate a multi-beam system for characterizing particles in accordance with the present invention.
Figure 12B:
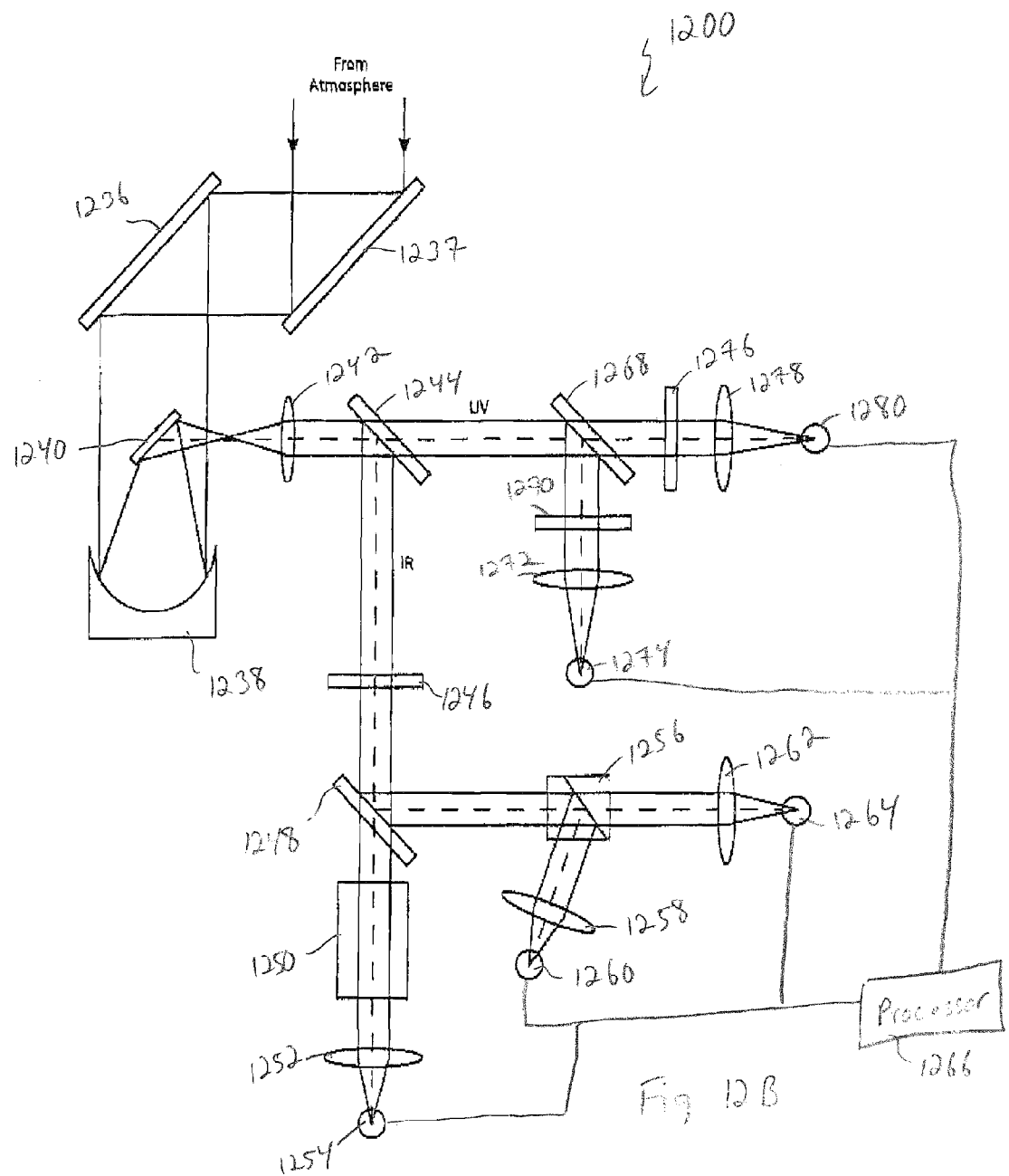

FIG. 11A shows the total backscatter intensity of two additional plumes, distinct from those detected in FIGS. 9A, 9B, 10A and 10B, located between about one and two kilometers away from the system. Feature 1101 represents the detection of a plume of BG from an aerial release over the test range. Feature 1102 represents the detection of a point release of male specific bacteriophage type 2 (MS2), which is representative of viral agents.

FIG. 11B shows the results of detecting the same atmospheric features as in FIG. 11A with an embodiment of the present invention. Feature 1104 is a result of detecting the same plume depicted by feature 1102 in FIG. 11A. However, feature 1104 depicts depolarization ratio, not the total backscatter intensity. The relatively darker color of feature 1104, as compared to the background of the image, indicates that the MS2 had a lower depolarization ratio then the background. Feature 1103 is a result of detecting the same plume depicted by feature 1101 in FIG. 11A. The relatively lighter color of feature 1103, as compared to the background of the image, indicates that the BG had a higher depolarization ratio than the background.

The experiment results depicted in FIGS. 11A and 11B confirmed that an embodiment of the present invention is capable of distinguishing between types of aerosol particles based on depolarization characteristics.

In the embodiments described above, aerosol particles have been characterized based on polarization phenomenon. It will be appreciated, however, that various optical parameters may be utilized to identify and characterize aerosol particles. A further exemplary system 1200 is shown in FIGS. 12A and 12B in this regard. The system 1200 is a multiple beam system that uses induced fluorescence to determine at least one characteristic of aerosol particles. Laser induced fluorescence has previously been used as a stand-alone technique for detection of bioaerosols. The technique works by employing a pulsed laser at an ultraviolet wavelength, typically 355 nm-266 nm. UV pulses transmitted into the atmosphere cause biological particles to fluoresce. The fluorescence occurs over a relatively broad band of wavelengths but is typically strongest between 400-450 nanometers. The fluorescence can be detected by a lidar receiver, and range information can be obtained based on the time elapsed between the laser transmission and the received signal. The illustrated system 1200 employs an eye-safe beam such as described above together with a UV beam to identify and characterize particle structures of interest. Molecular backscatter of the IR and UV beams, polarization phenomena and fluorescence can be used to characterize the particles. Alternatively, the IR and UV beams can be used sequentially. In the latter regard, the eye-safe IR beam can first be used to identify a particle structure of interest. Once such a structure of interest is identified, a second beam may be utilized to induce fluorescence and characterize the particles of interest. The second beam may or may not be eye-safe, depending on the application. In any event, significant advantages are achieved by using the eye-safe lidar at least for initial detection.

The illustrated system 1200 includes a master oscillator 1202 for providing a source beam. For example, the master oscillator 1202 may be an Nd:YAG, as described above. A seed laser 1204 may be utilized to provide a higher quality source beam. For example, the seed laser 1204 may be a 1064 nm fiber injection seed laser. The outputs from the master oscillator 1202 and seed laser 1204 are combined using mirror 1203 and combiner 1201. In this regard, it will be appreciated that the combiner 1201 transmits the output from the master oscillator 1204 and coaxially reflects the output from the seed laser 1204.

The combined beam is then processed by amplifiers 1206 to provide an input beam of the desired power. In the illustrated embodiment, the amplified beam is then redirected by mirrors 1207 and 1208 and is split by beam splitter 1209. The beam splitter 1209 transmits a desired portion of the signal and reflects the remainder of the signal to mirror 1210. The first portion of the signal is transmitted to a Raman cell 1222, which is operative to provide an output beam having significant energy in the desired wavelength range, e.g., in the 1.5-1.8 micron range. A wavelength-dependent beam separator 1224, such as a Pellin Broca prism, separates the eye-safe beam from the remaining non-eye-safe beam component. The non-eye-safe beam component is directed to a beam dump (1228), which absorbs or otherwise eliminates this unwanted component.

The remaining portion of the beam that is redirected by separator 1209 is redirected by mirror 1210 to a frequency doubler 1212 and a frequency tripler 1214. If desired, a frequency quadrupler or the like (not shown) may also be provided. The frequency adjusted output is then redirected by mirrors 1226 and 1230 to beam combiner 1232. In the illustrated embodiment, as a result of the operation of the Raman cell 1222 and the frequency doubler and tripler 1212 and 1214, the combiner 1232 receives one infrared beam and one ultraviolet beam. The combiner 1232 is operative to transmit the ultraviolet beam and reflect the infrared beam so that the beams are coaxially combined. The combined beam is then transmitted through a beam expander 1234. This beam expander reduces the intensity of the beam. In this manner, at least the infrared beam is maintained at an eye-safe level. For certain applications, the ultraviolet portion of the beam may also be eye-safe. The beam is then output to the atmosphere via mirrors 1235-1237.

Although this system is thus shown as outputting a combined infrared and ultraviolet beam, it will be appreciated that these beams may be used in alternating fashion. For example, it may be desired to use the eye-safe infrared beam to detect aerosol structures of interest. Upon identification of an aerosol structure of interest, the ultraviolet beam may be activated to induce fluorescence so that the aerosol particles can be characterized, e.g., as being benign or potentially harmful. In this regard, separate sources may be used for the infrared and ultraviolet beams. Alternatively, a single source may be used as illustrated. However, a movable mirror, a shutter or the like may be used to selectively transmit one or both of the infrared and ultraviolet components.

FIG. 12B illustrates the receiver components of the system 1200. In this regard, radiation from the atmosphere, which may include molecular backscattered IR and UV radiation, backscattered polarized radiation and radiation due to induced fluorescence, is directed by mirrors 1236-1237 to a telescope primary mirror 1238. The telescope primary mirror 1238 redirects the incoming radiation to the telescope secondary mirror 1240, which, in turn, redirects the radiation to a beam splitter 1244 via collimating lens 1242, which is operative to collimate both the UV and IR components. In the illustrated embodiment, the beam splitter 1244 is a shortwave pass dichroic, which is operative to pass the UV component and reflect the infrared component. The UV component that is transmitted by the beam splitter 1244 is incident on a further beam splitter 1268, which is operative to separate the fluorescence from the UV molecular and aerosol backscatter. Specifically, the fluorescence is reflected to a fluorescence detector 1274 via an interference filter 1270 and a focusing lens 1272. The UV molecular and aerosol backscatter is transmitted from the beam splitter 1268 to a UV molecular backscatter detector 1280 via an interference filter 1276 and focusing lens 1278. Additional optical components could replace components 1276, 1278 and 1280 in order to separate and detect molecular and aerosol backscattering.

The infrared portion of the signal reflected by beam splitter 1244 is directed to beam splitter 1248 via interference filter 1246. The beam splitter 1248 is operative to separate the infrared molecular backscatter from the polarized backscatter of interest. In particular, the molecular backscatter is transmitted to a molecular backscatter detector 1254 via a hydrogen cyanide absorption filter 1250 and a focusing lens 1252.

The polarized backscatter of interest is redirected to a polarization beam splitter 1256. The polarization beam splitter 1256 is operative to separate parallel polarized radiation from perpendicular polarized radiation. In this regard, the perpendicular polarized radiation is redirected to perpendicular polarization detector 1236 via focusing lens 1258. The parallel polarized radiation is transmitted to parallel polarization detector 1264 via focusing lens 1262.

The outputs from all of the detectors (1274, 1280, 1254, 1260 and 1264) are provided to a processor 1266, which is operative to process the signals to characterize the aerosol particles of interest. In this regard, aerosol particle types of interest may be studied to develop particle type signatures, which may be expressed in relation to the detected parameters. For example, anthrax may have a different signature with respect to the detected parameters than common industrial effluents. The signatures may be represented as values in look-up tables. Thus, the processor 1266 is operative to analyze the inputs from the various detectors (1254, 1260, 1264, 1274 and 1280) and to access the look-up tables based on the measured values. The processor can then output information regarding the detected particles, such as the likely particle type, composition or other characteristics of the particle.

While various embodiments of the present invention have been described in detail, it is apparent that further modifications and adaptations of the invention will occur to those skilled in the art. However, it is to be expressly understood that such modifications and adaptations are within the spirit and scope of the present invention.

What is claimed:

1. A lidar system to remotely identify aerosol particles comprising:

a transmitter for transmitting into an atmosphere an optical beam wherein said optical beam is substantially linearly polarized in a single polarization plane;

a receiver for receiving backscattered radiation of said optical beam and directing said backscattered radiation onto at least one detector, said at least one detector being operative for converting said backscattered radiation into at least one electrical signal representative of said backscattered radiation; and a processor to determine at least one characteristic of said aerosol particles based on analysis of said at least one electrical signal, wherein said receiver comprises:

a. collection optics for collecting said backscattered radiation;

b. a collimator for collimating said backscattered radiation interposed between said collection optics and said at least one detector;

c. a beam-splitter for splitting said collimated backscattered radiation into a first post-beam-splitter beam and a second post-beam-splitter beam, wherein said first post-beam-splitter beam is linearly polarized in a single polarization plane that is substantially parallel to the polarization plane of said transmitted optical beam, and wherein said second post-beam-splitter beam is linearly polarized in a single polarization plane that is substantially perpendicular to the polarization plane of said transmitted optical beam;

d. first directing optics for directing said first post-beam-splitter beam onto a first detector, said first detector being operative for converting said first post-beam-splitter beam into a first electrical signal representative of said first post-beam-splitter beam; and e. second directing optics for directing said second post-beam-splitter beam onto a second detector, said second detector being operative for converting said second post-beam-splitter beam into a second electrical signal representative of said second post-beam-splitter beam.

2. A lidar system as set forth in claim 1, wherein said optical beam has a primary wavelength between about 1.5-1.8 microns.

3. A lidar system to remotely identify aerosol particles comprising:

a transmitter for transmitting into an atmosphere an optical beam wherein said optical beam is substantially linearly polarized in a single polarization plane;

a receiver for receiving backscattered radiation of said optical beam and directing said backscattered radiation onto at least one detector said at least one detector being operative for converting said backscattered radiation into at least one electrical signal representative of said backscattered radiation; and a processor to determine at least one characteristic of said aerosol particles based on analysis of said at least one electrical signal, wherein said transmitter comprises at least one thin film plate polarizer placed in the path of said optical beam.

4. A lidar system as set forth in claim 3, wherein the portion of said optical beam reflected off of said at least one thin film plate polarizer closest along the beam path to the beam source is directed to a beam dump.

5. A lidar system as set forth in claim 3, wherein said transmitter further comprises a Faraday isolator located in the path of said optical beam.

6. A lidar system as set forth in claim 1, wherein said transmitter comprises a laser pump for providing a source beam having a source wavelength and a Raman wavelength shifter for shifting said source wavelength from said source wavelength to a second wavelength.

7. A lidar system as set forth in claim 6, wherein said Raman wavelength shifter comprises:

coating-free interior reflective elements;

optical surfaces oriented at Brewster angle; and multiple passes of said optical beam are completed by total internal reflections from interior prisms.

8. A lidar system as set forth in claim 1, wherein said receiver has a field of view of at most 0.5 mrad Full-angle.

9. A lidar system as set forth in claim 1, wherein said receiver has a field of view of at most 0.4 mrad Full-angle.

10. A lidar system as set forth in claim 1, wherein said beam-splitter is a Glan-Taylor Calcite air-spaced beam-splitter cube with one side exit and a single layer anti-reflective coating for use at the wavelength of said transmitted optical beam.

11. A lidar system as set forth in claim 1, wherein said receiver further comprises a ½ wave plate mounted in a rotary mount interposed between said collimator and said beam-splitter.

12. A lidar system as set forth in claim 11, wherein said ½ wave plate can be selectively oriented to have no substantial effect on said collimated backscattered radiation or to convert all of said collimated backscattered radiation into a beam that is circularly polarized.

13. A lidar system as set forth in claim 1, wherein said receiver comprises a processor being operative for comparing said first electrical signal to said second electrical signal and calculating a ratio of said second electrical signal to said first electrical signal.

14. A lidar system as set forth in claim 1, further comprising a scanner for scanning said optical beam relative to at least one scan axis.

15. A lidar system as set forth in claim 14, wherein said scanner is operative to scan said optical beam relative to two axes.

16. A lidar system as set forth in claim 1, wherein said processor is operative for comparing parameters of said backscattered radiation to a database of parameters correlated to known particles to identify said aerosol particles.

17. A lidar system to remotely identify aerosol particles comprising:
- a transmitter for transmitting into an atmosphere an optical beam of known polarization;
- a receiver for receiving at least one return signal resulting from said transmission;
- at least one detector being operative for converting said at least one return signal into at least one electrical signal representative of said at least one return signal; and
- a processor to determine at least one characteristic of said aerosol particles based on analysis of polarization characteristics of said at least one return signal, wherein said processor is operative for comparing parameters of said at least one return signal to a database of parameters correlated to known particles to identify said aerosol particles;
- wherein said receiver further comprises a beam splitter to split said return signal into:
- a first post-beam-splitter beam which is linearly polarized in a single polarization plane that is substantially parallel to the polarization plane of said transmitted optical beam and
- a second post-beam-splitter beam which is linearly polarized in a single polarization plane that is substantially perpendicular to the polarization plane of said transmitted optical beam.

18. A lidar system as set forth in claim 17, wherein said transmitted optical beam is substantially linearly polarized in a single polarization plane.

19. A lidar system as set forth in claim 17, wherein said lidar system is capable of determining said at least one characteristic of said aerosol particles from substantially a single pulse of said transmitted optical beam, wherein said optical beam has a primary wavelength between about 1.5-1.8 microns furthermore wherein said optical beam has a pulse energy of at least 200 mJ per pulse and an energy flux of at most 0.1 W/cm$^2$.

20. A lidar system to remotely identify at least one characteristic of atmospheric aerosol particles comprising:
- a transmitter for transmitting at least a first, eye-safe optical beam;
- a receiver for receiving backscattered radiation of said at least first optical beam and directing said backscattered radiation onto at least one detector;
- said at least one detector being operative for converting said backscattered radiation into at least one electrical signal representative of said backscattered radiation; and
- a processor to determine at least one characteristic of said aerosol particles based on analysis of said at least one electrical signal;
- wherein said receiver further comprises a beam splitter to split said return signal into:
- a first post-beam-splitter beam which is linearly polarized in a single polarization plane that is substantially parallel to the polarization plane of said transmitted optical beam and
- a second post-beam-splitter beam which is linearly polarized in a single polarization plane that is substantially perpendicular to the polarization plane of said transmitted optical beam.

21. A lidar system as set forth in claim 20, wherein said transmitted optical beam is substantially linearly polarized in a single polarization plane.

22. A lidar system as set forth in claim 20, wherein said optical beam has a primary wavelength between about 1.5-1.8 microns, wherein said optical beam has a pulse energy of at least 200 mJ per pulse, wherein said optical beam has an energy flux of at most 0.1 W/cm$^2$.

23. A lidar system as set forth in claim 20, wherein said processor is operative for comparing parameters of said at least one electrical signal to a database of parameters correlated to known particles to identify said aerosol particles.

24. A lidar system as set forth in claim 23, wherein said processor determines said at least one characteristic based on analysis of said at least one electrical signal from substantially a single pulse of said transmitted optical beam.

25. A lidar system as set forth in claim 23, wherein said processor is operative to distinguish between a first particle type and a second particle type where the first particle type has a different chemical composition than said second particle type.

26. A lidar system as set forth in claim 23, wherein said transmitter is operative to transmit said first beam and a second beam having different optical properties than said first beam.

27. A lidar system as set forth in claim 26, wherein said second beam is an eye-safe beam.

28. A lidar system as set forth in claim 26, wherein said processor uses an electrical signal corresponding to said second beam to determine said at least one characteristic.

29. A lidar system as set forth in claim 26, wherein said processor is operative to process information related to said first beam and based thereon to make a determination regarding transmission of said second beam.

30. A transmitter for transmitting an optical beam comprising:
- a laser pump for generating a source beam, wherein said source beam is generated having a first nominal wavelength;
- beam directing optics for directing said source beam from near ground elevation into the atmosphere;
- a beam processor operatively interposed between said laser pump and said beam directing optics to modify said source beam to achieve single-plane linear polarization and a nominal wavelength between about 1.5-1.8 microns, and
- a Raman wavelength shifter, operatively interposed between said laser pump and said beam directing optics, to shift said source beam to a second nominal wavelength between about 1.5-1.8 microns wherein said Raman wavelength shifter comprises:
- coating-free interior reflective elements;
- optical surfaces oriented at Brewster angle; and multiple passes of said optical beam are completed by total internal reflections from interior prisms.

31. A transmitter as set forth in claim 30, wherein said beam processor comprises at least one thin film plate polarizer placed in the path of said source beam to achieve single-plane polarization of said transmitted optical beam.

32. A transmitter as set forth in claim 31, wherein the portion of said optical beam reflected off of said at least one thin film plate polarizer closest along the beam path to said laser pump is directed to a beam dump.

33. A transmitter as set forth in claim 31, wherein said transmitter further comprises a Faraday isolator located in the path of said optical beam.

34. A transmitter as set forth in claim 30, further comprising a scanner for scanning said transmitted optical beam relative to at least one scan axis.

35. A transmitter as set forth in claim 34, wherein said scanner is operative to scan said transmitted optical beam relative to two axes.

36. A receiver comprising:
collection optics for receiving backscattered radiation of a transmitted single-plane linearly polarized optical beam having a primary wavelength between about 1.5-1.8 microns;
a collimator for collimating said backscattered radiation interposed between said collection optics and a beam splitter;
said beam-splitter for splitting said collimated backscattered radiation into a first post-beam-splitter beam which is linearly polarized in a single polarization plane and a second post-beam-splitter beam which is linearly polarized in a single polarization plane that is substantially perpendicular to the polarization plane of said first post-beam-splitter beam, wherein said first post-beam-splitter beam is in a known polarization plane orientation relative to the transmission plane of said transmitted optical beam;
first directing optics for directing said first post-beam-splitter beam onto a first detector, said first detector being operative for converting said first post-beam-splitter beam into a first electrical signal representative of said first post-beam-splitter beam; and
second directing optics for directing said second post-beam-splitter beam onto a second detector, said second detector being operative for converting said second post-beam-splitter beam into a second electrical signal representative of said second post-beam-splitter beam
wherein said receiver has a field of view of at most 0.5 mrad.

37. A receiver as set forth in claim 36, wherein said receiver has a field of view of at most 0.2 mrad.

38. A receiver as set forth in claim 36, wherein said beam-splitter is a Glan-Taylor Calcite air-spaced beam-splitter cube with one side exit and a single layer anti-reflective coating for use at the wavelength of said transmitted optical beam.

39. A receiver as set forth in claim 36, wherein said receiver further comprises a ½ wave plate mounted in a rotary mount interposed between said collimator and said beam-splitter.

40. A receiver as set forth in claim 39, wherein said ½ wave plate can be selectively oriented to have no substantial effect on said collimated backscattered radiation or to convert all of said collimated backscattered radiation into a beam that is circularly polarized.

41. A receiver as set forth in claim 36, wherein said receiver comprises a processor being operative for comparing said first electrical signal to said second electrical signal and calculating a ratio of said second electrical signal to said first electrical signal.

42. A method for remotely distinguishing aerosol particles, comprising the steps of:
transmitting a beam of radiation of known polarization into an atmosphere;
receiving backscattered radiation that has interacted with aerosol particles in the atmosphere as a result of said transmitting; and
analyzing at least one polarization characteristic of the received backscattered radiation to distinguish between first and second particle types where the first and second particle types differ with respect to chemical composition, wherein said analyzing at least one polarization characteristic comprises comparing backscattered radiation linearly polarized in a plane substantially perpendicular to the polarization plane of the transmitted optical beam to backscattered radiation linearly polarized in a plane substantially parallel to the polarization plane of the transmitted optical beam.

43. A method as set forth in claim 42, wherein said transmitting is at a primary wavelength between about 1.5-1.8 microns.

44. A method for remotely identifying aerosol particles, comprising the steps of:
transmitting a single-plane linearly polarized optical beam into an atmosphere;
receiving backscattered radiation of said single-plane linearly polarized optical beam; and
analyzing polarization attributes of said backscattered radiation to characterize said aerosol particles with respect to chemical composition, wherein said analyzing of polarization attributes comprises calculating the ratio of backscattered radiation linearly polarized in a plane substantially perpendicular to the polarization plane of the transmitted optical beam to backscattered radiation linearly polarized in a plane substantially parallel to the polarization plane of the transmitted optical beam.

45. A method as set forth in claim 44, wherein said transmitting is at a primary wavelength between about 1.5-1.8 microns.

46. A method as set forth in claim 44 wherein said analyzing of polarization attributes further comprises comparing said polarization attributes to a database correlating particular polarization attributes to particular aerosol particles.

47. A method as set forth in claim 44, further comprising comparing said ratio to a database containing data that correlates particular ratios to particular aerosol particles.

48. A method of processing backscattered radiation from a single-plane linearly polarized optical beam source having a primary wavelength of between about 1.5-1.8 microns, comprising the steps of:
receiving said backscattered radiation;
collimating said backscattered radiation;
splitting said backscattered radiation into a first linearly polarized beam of known orientation relative to the transmission plane of said optical beam and a second linearly polarized beam whose linear polarization is substantially perpendicular to the polarization plane of the first linearly polarized beam;

focusing said first linearly polarized beam onto a first detector surface to provide a first electrical signal representative of said first linearly polarized beam;

focusing said second linearly polarized beam onto a second detector surface to provide a second electrical signal representative of said second linearly polarized beam; and calculating the ratio of backscattered radiation detected whose linear polarization is in a plane perpendicular to the polarization plane of the transmitted beam to backscattered radiation detected whose linear polarization is in a plane parallel to the polarization plane of the transmitted beam.

49. A method as set forth in claim 48, further comprising comparing said ratio to a database correlating particular ratios to particular sources of backscattered radiation to identify a source of the backscattered radiation.

* * * * *

UNITED STATES PATENT AND TRADEMARK OFFICE
CERTIFICATE OF CORRECTION

PATENT NO.       : 7,580,127 B1  
APPLICATION NO.  : 11/459267  
DATED            : August 25, 2009  
INVENTOR(S)      : Mayor et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 264 days.

Signed and Sealed this

Fourteenth Day of September, 2010

David J. Kappos  
*Director of the United States Patent and Trademark Office*